United States Patent
Biber

(10) Patent No.: US 12,372,594 B2
(45) Date of Patent: Jul. 29, 2025

(54) DENTAL COIL FOR A MAGNETIC RESONANCE SYSTEM

(71) Applicant: Siemens Healthcare GmbH, Erlangen (DE)

(72) Inventor: Stephan Biber, Erlangen (DE)

(73) Assignee: Siemens Healthineers AG, Erlangen (DE)

( * ) Notice: Subject to any disclaimer, the term of this patent is extended or adjusted under 35 U.S.C. 154(b) by 149 days.

(21) Appl. No.: 18/255,410

(22) PCT Filed: Nov. 5, 2021

(86) PCT No.: PCT/EP2021/080797
§ 371 (c)(1),
(2) Date: Jun. 1, 2023

(87) PCT Pub. No.: WO2022/122269
PCT Pub. Date: Jun. 16, 2022

(65) Prior Publication Data
US 2024/0094318 A1 Mar. 21, 2024

(30) Foreign Application Priority Data
Dec. 7, 2020 (DE) .......................... 102020215396.5

(51) Int. Cl.
*G01R 33/34* (2006.01)
*A61B 5/00* (2006.01)
(Continued)

(52) U.S. Cl.
CPC ........ *G01R 33/34084* (2013.01); *A61B 5/055* (2013.01); *A61B 5/4542* (2013.01); *G01R 33/341* (2013.01); *G01R 33/3621* (2013.01)

(58) Field of Classification Search
CPC ............ G01R 33/34084; G01R 33/341; G01R 33/3621; G01R 33/34007; G01R 33/3415; G01R 33/365; A61B 5/055; A61B 5/4542
See application file for complete search history.

(56) References Cited

U.S. PATENT DOCUMENTS 7,382,132 B1 6/2008 Mathew et al.
2012/0146645 A1 6/2012 Rasche et al.
(Continued)

FOREIGN PATENT DOCUMENTS

DE 102009027119 A1 12/2010
EP 3489704 A1 5/2019

OTHER PUBLICATIONS

English translation of EP-3489704-A1 (Year: 2019).*
(Continued)

*Primary Examiner* — G.M A Hyder
(74) *Attorney, Agent, or Firm* — Banner & Witcoff Ltd.

(57) ABSTRACT

The disclosure relates to a dental coil comprising a transmitter unit including an antenna, a receiver unit with an array of antennas, and a carrier element to be positioned in use on the jaw region of the patient and to follow at least part of the outer shape of the jaw region of the patient, wherein the carrier element is moreover designed to hold the array of antennas of the receiver unit in a predetermined relative position with respect to the jaw region of the patient, such that the array of antennas of the receiver unit borders the outer shape of the jaw region in the predetermined relative position. The disclosure further relates to a magnetic resonance system having a magnetic resonance apparatus and a dental coil, wherein the magnetic resonance apparatus is designed to detect magnetic resonance signals from a jaw region of the patient via the dental coil.

15 Claims, 8 Drawing Sheets

(51) Int. Cl.
   A61B 5/055      (2006.01)
   G01R 33/341     (2006.01)
   G01R 33/36      (2006.01)

(56) References Cited

U.S. PATENT DOCUMENTS

| | | |
|---|---|---|
| 2012/0288820 A1 | 11/2012 | Choe et al. |
| 2013/0190608 A1 | 7/2013 | Schmidt |
| 2013/0252196 A1 | 9/2013 | Rasche et al. |
| 2021/0018579 A1* | 1/2021 | Nixdorf .............. A61C 9/0046 |

OTHER PUBLICATIONS

Gradl J. et al: "Application of a Dedicated Surface Coil in Dental MRI Provides Superior Image Quality in Comparison with a Standard Coil"; Clinical Neuroradiology, Springer Berlin Heidelberg, Berlin/Heidelberg; vol. 27, No. 3, Feb. 11, 2016 (Feb. 11, 2016), pp. 371-378, XP036308711.
Ludwig, Ute et al. "Dental MRI Using Wireless Intraoral Coils", 2016, Scientific Reports, https://www.ncbi.nlm.nih.gov/pmc/articles/PMC4810435/.
Prager, Marcel et al: "Dental MRI Using a Dedicated RF-Coil at 3 Tesla", Journal of Cranio-Maxillo-Facial Surgery, Churchill Livingstone, GB; vol. 43, No. 10, Oct. 22, 2015 (Oct. 22, 2015 ), pp. 2175-2182, XP029341836.
Bendszus et al. "Mandibula 15-Kanal Dental Spule", 2020, Noras MRI products, https://www.noras.de/mri-produkte/mandibula-15-ch-dental-spule/.
Feb. 3, 2022 (PCT) International Search Report—App. PCT/EP2021/080797.

* cited by examiner

DENTAL COIL FOR A MAGNETIC RESONANCE SYSTEM

CROSS-REFERENCE TO RELATED APPLICATIONS

The present application is a U.S. National Stage entry of PCT Application no. PCT/EP2021/080797, filed Nov. 5, 2021, which claims priority to and the benefit of Germany patent application no. DE 10 2020 215 396.5, filed on Dec. 7, 2020, the contents of each of which are incorporated herein by reference in their entireties.

TECHNICAL FIELD

The disclosure relates to a dental coil comprising a transmitter unit with at least one antenna, a receiver unit with an array of antennas, and a carrier element. The disclosure further relates to a magnetic resonance system comprising a magnetic resonance apparatus and a dental coil, wherein the magnetic resonance apparatus is designed to acquire magnetic resonance signals of a patient's jaw region by means of the dental coil.

BACKGROUND

Diseases of the teeth and periodontium, such as caries or periodontitis, are nowadays usually diagnosed using X-ray-based imaging methods. Conventional or digital X-ray projection methods are mainly used, as well as, more recently, three-dimensional X-ray methods. An example of a three-dimensional X-ray technique is digital volume tomography, which can be used for imaging teeth and the viscerocranium.

A major disadvantage of X-ray methods is that it is necessary to use ionizing radiation for imaging. An imaging technique that does not involve ionizing radiation is magnetic resonance imaging. This typically provides better soft tissue contrast than X-ray methods and supports three-dimensional imaging of an object under examination as standard. In addition, magnetic resonance imaging allows cysts to be imaged and dentin degradation to be detected before it can be detected by X-ray. Magnetic resonance imaging thus represents a potential alternative to known X-ray methods for imaging a region of dentition and/or a region of the jaw and for diagnosing dental diseases of the object under examination.

SUMMARY

Magnetic resonance imaging is a well-known imaging technique for generating magnetic resonance images of the interior of an object under examination. To perform magnetic resonance imaging, the object under examination is usually positioned in a strong, static and homogeneous main magnetic field (B0 field) of a magnetic resonance apparatus. The main magnetic field can have magnetic field strengths of 0.2 to 7 Tesla, so that nuclear spins of the object under examination align along the main magnetic field. To trigger so-called nuclear spin resonances, radiofrequency signals known as excitation pulses (B1 field) are applied to the object under examination. Each excitation pulse causes the magnetization of particular nuclear spins of the object under examination to deviate from the main magnetic field by an amount which is known as the flip angle. An excitation pulse can have an alternating magnetic field with a frequency corresponding to the Larmor frequency at the respective static magnetic field strength. The excited nuclear spins can exhibit a rotating and decaying magnetization (nuclear spin resonance) which can be detected as a magnetic resonance signal by means of special antennas. Magnetic gradient fields can be superimposed on the static magnetic field to spatially encode the nuclear magnetic resonances of the object under examination.

The received magnetic resonance signals are typically digitized and stored as complex values in a k-space matrix. This k-space matrix can be used as the basis for reconstructing magnetic resonance images as well as for determining spectroscopy data. The magnetic resonance image is typically reconstructed by means of a multidimensional Fourier transform of the k-space matrix.

As it does not involve ionizing radiation, magnetic resonance imaging is particularly suitable for continuous diagnostic monitoring of dental disease and/or tooth development as part of a longitudinal imaging study. In longitudinal imaging studies, a plurality of imaging examinations are usually performed to determine the progression of a disease or the success of a therapeutic treatment over a predetermined period of time. However, diagnostically relevant areas of a patient's jaw region, such as the oral cavity, dentition, dental arch or tooth, provide a small volume for generating magnetic resonance signals. Moreover, conventional volume and surface coils, such as head coils and lay-on coils, are at a relatively large distance from the diagnostically relevant area. The achievable distances can be too large to acquire high-quality magnetic resonance images of the patient's dentition.

The object of the disclosure is therefore to provide a dental coil which enables magnetic resonance images of the patient's jaw region to be acquired with high quality. This object is inventively achieved as described herein, including the claims.

The dental coil according to the disclosure comprises a transmitter unit and a receiver unit, wherein the transmitter unit has at least one antenna which is designed to transmit radiofrequency signals in a frequency and power range of the magnetic resonance apparatus into a patient's jaw region, and wherein the receiver unit has an array of antennas which is designed to receive magnetic resonance signals from the patient's jaw region.

An antenna of the local coil according to the disclosure can be a coupling element between electromagnetic waves guided in signal conductors and unguided, i.e. in free space. An antenna of the receiver unit is preferably designed to receive electromagnetic waves in the magnetic resonance frequency range of an MR-active atomic nucleus. For example, an electromagnetic wave with a frequency of between 1 and 500 MHz, preferably between 10 and 300 MHz, is regarded as a radiofrequency signal. The magnetic resonance signal of usual atomic nuclei under examination can have a low power of a few microwatts to several milliwatts. The at least one antenna of the transmitter unit can be designed to emit a radiofrequency signal into the patient's jaw region. The radiofrequency signal emitted by the at least one antenna of the transmitter unit can range in power from a few watts to several kilowatts depending on the main magnetic field of a magnetic resonance apparatus.

A signal conductor is preferably an electrically conductive wire. The wire of the signal conductor can have an oval or polygonal cross-section which is suitable for continuously carrying the powers specified above. It is conceivable for the signal conductor to be implemented as a conductor track on a printed circuit board and to have an approximately rectangular cross-section. The signal conductor can be made of copper. However, other electrically conductive metals, such as gold or aluminum, are also conceivable. Preferably, each antenna of the receiver unit and/or the transmitter unit has a signal conductor.

An antenna of the dental coil according to the disclosure preferably has contact protection to shield the object under examination from voltages and/or burns. For this purpose, the signal conductor of the antenna can have e.g. a plastic coating and/or covering. Suitable plastics include polytetrafluoroethylene (PTFE) or various polysiloxanes. A current can be induced in a signal conductor of the receiver unit by a nuclear magnetic resonance, which current can be detected as a magnetic resonance signal by the magnetic resonance apparatus. On the other hand, an alternating current can be applied to a signal conductor of the transmitter unit in order to transmit a radiofrequency signal, the so-called B1 magnetic field, into the patient's jaw region.

For signal transmission, the array of antennas of the receiver unit and the at least one antenna of the transmitter unit are preferably electrically connected to the magnetic resonance apparatus. It is conceivable for the electrical connection between the array of antennas of the receiver unit and/or of the at least one antenna of the transmitter unit to the magnetic resonance apparatus to be established via an electrical connecting cable. Such an electrical connecting cable can be e.g. a coaxial cable that is shielded to prevent electromagnetic interference from the environment.

It is also conceivable for the receiver unit and/or the transmitter unit to comprise an electronic circuit which is connected to an antenna. The electronic circuit can comprise an electronic component or a combination of a plurality of electronic components such as transistors, resistors, capacitors, diodes, conductor tracks and the like. In particular, the electronic circuit can have a protection circuit designed to provide an antenna with overload protection. To prevent magnetic attraction forces, standing waves, heating and similar undesirable effects, the electronic circuit can have a high proportion of non-magnetic materials and appropriate sheath current filters and/or baluns. The electronic circuit preferably comprises a printed circuit board (PCB) or a comparable substrate suitable for accommodating the electronic components in a predetermined position relative to one another.

The dental coil according to the disclosure comprises a carrier element which is appropriately positioned for use on the patient's jaw region and is molded to match at least part of the outer shape of the patient's jaw region, wherein the carrier element is designed to maintain the array of antennas of the receiver unit in a predetermined relative position with respect to the patient's jaw region and wherein the array of antennas of the receiver unit surrounds the outer shape of the jaw region in the predetermined relative position. A carrier element preferably provides a supporting structure for the array of antennas of the receiver unit and is connected thereto. The carrier element can be connected to the array of antennas in any form-fit, force-fit and/or integrally bonded manner. It is conceivable for the array of antennas to be glued and/or screwed to the carrier element. However, the array of antennas can also be embedded, clipped, clamped or slotted into the carrier element and/or welded thereto. The connection to the carrier element can in particular increase the structural stability of the array of antennas.

The array of antennas of the receiver unit preferably comprises between four and twelve antennas. In a preferred embodiment, the array of antennas comprises eleven or twelve antennas. In particular, the array of antennas can be in a 5-7 configuration, a 3-9 configuration, or a 6-6 configuration. For example, in the 5-7 configuration, with the carrier element appropriately positioned for use on the patient's jaw region, five antennas are disposed along the dental arch of the patient's maxilla, while seven antennas are disposed along the dental arch of the patient's mandible. In addition, other configurations, such as a 5-5, a 4-6 or a 4-6-1 configuration, are self-evidently also conceivable. In a 4-6-1 configuration, one antenna can be positioned centrally in front of a region of the patient's mouth, while four antennas are disposed along the dental arch of the patient's maxilla and six antennas along the dental arch of the patient's mandible.

The antennas can have an approximately polygonal or oval shape, in particular an elliptical or circular shape. Circular antennas can have a diameter of between 3 and 8 cm. Antennas of a different shape can have an area equivalent to a circular antenna with a diameter of between 3 and 8 cm. The antennas of the receiver unit are preferably disposed in an offset and partially overlapping manner along the main extent of the carrier element. By matching the shape of the carrier element to the outer shape of the patient's jaw region, the antennas can be positioned in a predetermined relative position with respect to the patient's jaw region and surround it. In one embodiment, the array of antennas of the receiver unit is shaped to match the outer shape of the patient's jaw region by means of the carrier element. It is conceivable for the carrier element and/or the array of antennas of the receiver unit, when appropriately positioned for use on the patient's jaw region, to have a plane of symmetry corresponding to the patient's sagittal plane. The carrier element can be made of an electrically insulating material to protect the patient from voltage and/or burns. Preferably, the carrier element material is non-magnetic or exhibits low interaction with magnetic fields.

The carrier element is appropriately positioned for use on the patient's jaw region and is molded conformally to at least part of the outer shape of the patient's jaw region. This can mean that, in the position of use, the carrier element is shaped such that it replicates the outer shape of the patient's jaw region, e.g. the contour of the jawbone or of the skin surface of the jaw region. For example, two arbitrarily selected points on a side of the carrier element facing the patient can be approximately the same distance from the surface of the patient's jaw region when the carrier element is appropriately positioned for use on the patient along a normal vector through one of the two points in each case. In a preferred embodiment, the difference between the distances of the arbitrarily selected points from the surface of the patient's jaw region is less than one millimeter. However, it is equally conceivable for the difference in the distances of the arbitrarily selected points from the surface of the patient's jaw region to be a few millimeters, e.g. less than one millimeter, less than two millimeters, less than four millimeters, or less than ten millimeters. The absolute distance between any selected point on the patient-facing side of the carrier element when the carrier element is appropriately positioned for use on the patient along a normal vector through the selected point is preferably less than half a centimeter, less than three millimeters, less than two millimeters, or less than one millimeter from the surface of the patient's jaw region.

The carrier element is designed to maintain the array of antennas of the receiver unit in a predetermined relative position with respect to the patient's jaw region, wherein the array of antennas of the receiver unit surrounds the outer shape of the jaw region in the predetermined relative position. It is conceivable for a shape of the array of antennas of the receiver unit to conform to the shape of the carrier element which is molded to match at least part of the outer shape of the patient's jaw region. The contour of the carrier element preferably follows the contour of the jawbones and/or the contour of the skin surface of the jaw region, so that the array of antennas of the receiver unit is shaped according to the patient's jaw region. When the carrier element is appropriately positioned for use on the patient, the distance between any selected point on an antenna of the receiver unit along a normal vector through the any selected point can be less than three centimeters, less than 2.5 cm centimeters, or less than 2 cm centimeters from the support-element-facing surface of an incisor of the patient. The array of antennas of the receiver unit preferably surrounds at least an area of the patient's jaw region comprising a dental arch of the patient. However, it is equally conceivable for the array of antennas of the receiver unit to additionally also surround part of the patient's temporomandibular joint.

In one embodiment, the dental coil is designed to switch, within a short time, between transmitting radiofrequency signals by means of the transmitter unit and receiving magnetic resonance signals by means of the receiver unit. A short time can be, for example, a period of between 5 and 15 µs. Rapid switching between transmitting mode and receiving mode of the dental coil can advantageously support imaging of hard materials such as dentin, tooth enamel and/or the jawbone.

The dental coil according to the disclosure allows the array of antennas of the receiver unit to be positioned at a short distance from a diagnostically relevant area of the patient's jaw region, in particular the patient's dentition. This enables magnetic resonance signals to be advantageously received with a high signal-to-noise ratio despite the small signal volume of the patient's jaw region. In particular, the dental coil according to the disclosure allows imaging with a low main magnetic field strength of between 0.2 and 0.7 Tesla which usually involves low magnetization of jaw region tissue. This can advantageously contribute to the more widespread provision of dedicated magnetic resonance equipment in medical centers and/or smaller clinics where the use of a conventional magnetic resonance apparatus is not possible.

In one embodiment, the dental coil according to the disclosure comprises an adaptation element, wherein the carrier element has a flexible material, and wherein the adaptation element is designed to adjust a bending radius of the carrier element in order to match the shape of the array of antennas of the receiver unit to the external shape of the patient's jaw region.

A flexible material is preferably reversibly deformable. The carrier element can be made entirely of the flexible material or have segments of flexible material so that the carrier element can be molded to the external shape of the patient's jaw region. A reversibly deformable material can be plastically or elastically preformable. Examples of flexible materials include plastics such as polyethene, polyurethane, polyamide and polyester. In addition, natural-based materials such as rubber or fiber are also conceivable. The flexible material is preferably in the form of a foam, fibrous material or the like in order to achieve a low density and thus low weight. In one embodiment, the flexible material can be molded to the outer shape of the patient's jaw region by means of the adaptation element. For this purpose, the adaptation element can comprise a guide mechanism, a tensioning mechanism, a clamping mechanism, a bending mechanism, a traction mechanism or the like, which is designed to deform the carrier element in the position of use on the patient's jaw region and to adjust the bending radius of the carrier element according to the contour of the patient's jaw region. It is conceivable for the adaptation element to be mechanically connected to a mount which holds the carrier element in the position of use on the patient's jaw region.

Using an adaptation element enables the shape of the array of antennas of the receiver unit to be matched to the external shape of the patient's jaw region. As a result, the distance between the array of antennas of the receiver unit and the patient's jaw region can be advantageously reduced and the signal-to-noise ratio of the dental coil can be increased.

In one embodiment, the carrier element comprises a plastically deformable material that can be deformed manually to adjust the shape of the carrier element according to the external shape of the jaw region. A plastically deformable material can be any plastic or natural material which is plastically deformable by hand. By using a plastically deformable material, the carrier element can be advantageously adjusted to suit the individual shape of the patient's jaw region.

In another embodiment of the dental coil according to the disclosure, the carrier element comprises a dimensionally rigid material and has an articulation which divides the dimensionally rigid material of the carrier element into segments, wherein the articulation is designed to set the angle between two segments in order to set the relative position between at least one segment of the carrier element and at least one section of the patient's jaw region when the carrier element is appropriately positioned for use on the patient's jaw region.

A dimensionally rigid material can be any material which, when an external force is applied, substantially maintains a predetermined shape up to the point of fracture. However, it is equally conceivable for a dimensionally rigid material to be deformable, but require a force for the deformation thereof that exceeds proper manual handling of the carrier element. Examples of suitable rigid materials are plastics such as silicones, polyesters and polycarbonates, but also metals such as titanium and tantalum, and various ceramics such as aluminum and zirconium oxide. In addition, other materials are self-evidently also possible.

An articulation can have any mechanism that enables the angle between two segments of the carrier element to be adjusted. For example, an articulation can comprise a swivel joint, such as a roller hinge or a piano hinge, as well as a ball-and-socket joint. In addition, other types of articulations which allow the angle between two segments of the carrier element to be adjusted are of course also conceivable. The articulation preferably divides the carrier element into a series of segments along the main extent of the carrier element. It is conceivable for the carrier element to comprise one articulation or a plurality of articulations dividing the carrier element into two segments or into a plurality of segments. In a preferred embodiment, the articulation or plurality of articulations is spaced at a distance of several millimeters or several centimeters from an overlap region between two antennas of the array of antennas of the receiver unit. This prevents deformation of the overlap region between two antennas during adjustment of the shape of the carrier element to match the outer shape of the patient's jaw region. The overlap region between two antennas is preferably stabilized by the dimensionally rigid material of the carrier element so as to prevent relative movement between the two antennas. The array of antennas can be designed such that the centroid of an antenna is positioned at an articulation of the carrier element. The antenna can be reversibly deformed accordingly when the angle between two segments of the carrier element is adjusted. It is also conceivable for a signal conductor of the antenna to have a connecting element at the articulation of the carrier element, which enables or prevents bending or kinking of the signal conductor when the angle between two segments of the carrier element is adjusted by means of the articulation. In addition, two adjacent antennas can be inductively decoupled due to a predetermined overlap region between the two adjacent antennas. The carrier element can have a compensation mechanism that adjusts the overlap region between two adjacent antennas when adjusting the angle of the articulation so that inductive decoupling of the two adjacent antennas is maintained when the carrier element is deformed. In particular, the receiver unit in this embodiment can have an even number of antennas. Said overlap region between two adjacent antennas can be positioned at the mouth region, nose region and/or sagittal plane of the patient when the carrier element is in the position of use on the patient's jaw region.

In one embodiment, the articulation divides the carrier element into two mirror-symmetrical halves. In a position of use of the carrier element on the patient's jaw region, the articulation can be positioned at a mouth region, a nose region and/or the sagittal plane of the patient. It is conceivable for the receiver unit in this embodiment to have an odd number of antennas, wherein one antenna is positioned on the articulation at the mouth region or the nose region of the patient.

By using an articulation or a plurality of articulations, the array of antennas of the receiver unit can be advantageously adjusted to conform to the external shape of the patient's jaw region. In addition, by avoiding the positioning of articulations in an overlap region between two adjacent antennas, deformation of the overlap region can be reduced and/or prevented, so that potential impairment of the signal-to-noise ratio due to a changed inductive coupling between the two adjacent antennas can be advantageously avoided.

In one embodiment of the dental coil according to the disclosure, the carrier element is designed to maintain the at least one antenna of the transmitter unit in a predetermined relative position with respect to the patient's jaw region, wherein the transmitter unit is designed to generate radiofrequency signals with a magnetic field strength in the 20 to 80 µT range.

Similarly to the array of antennas of the receiver unit, the at least one antenna of the transmitter unit can also surround the outer shape of the patient's jaw region in the predetermined relative position. It is conceivable for the transmitter unit to have one antenna or a plurality of antennas that are molded conformally to the outer shape of the patient's jaw region in the predetermined relative position. The array of antennas of the receiver unit is preferably positioned between the patient's jaw region and the at least one antenna of the transmitter unit. This can mean that the at least one antenna of the transmitter unit is farther away from the patient's jaw region than the array of antennas of the receiver unit. The at least one antenna of the transmitter unit preferably has only a slightly higher volume requirement than the array of antennas of the receiver unit. It is conceivable for the dental coil to have an electrically insulating layer and/or an electrically insulating material which electrically separates the at least one antenna of the transmitter unit and the array of antennas of the receiver unit from one another.

By providing relatively high magnetic field strengths in the 20 to 80 µT range, comparatively high excitation of tissue in the patient's jaw region can be achieved. This advantageously allows the signal-to-noise ratio of received magnetic resonance signals to be increased. In addition, the time-averaged B1 magnetic field can be advantageously increased by means of relatively short excitation pulses having the above-mentioned magnetic field strength while complying with permissible limits for a specific absorption rate.

According to one embodiment, the transmitter unit comprises at least a first antenna and a second antenna, wherein the first antenna and the second antenna are disposed in an essentially circular and planar manner in parallel-aligned planes separate from one another such that a projection of a first surface enclosed by the first antenna along a normal vector of the first surface and of a second surface enclosed by the second antenna have a non-empty intersection, wherein the spacing corresponds to at least the width of the patient's jaw region, and wherein the normal vector of the first antenna is oriented essentially parallel to a frontal plane of the patient, wherein the carrier element is designed to maintain the transmitter unit in a predetermined relative position with respect to the patient's jaw region.

The signal conductors of the first antenna and the second antenna are preferably disposed in an approximately circular and planar manner in parallel-aligned planes separate from one another. The signal conductor of the first antenna and the signal conductor of the second antenna can be essentially aligned flush with one another. The width of the jaw region of the patient can be defined by a lateral distance between a point on a surface of a left cheek and a point on a surface of a right cheek of the patient. The distance between the first antenna and the second antenna is preferably slightly greater than the width of the patient's jaw region in order to allow for a volume for the array of antennas of the receiver unit and/or a predetermined distance of the dental coil from the surface of the patient's jaw region. The first antenna and the second antenna can be positioned in the predetermined relative position with respect to the patient's jaw region such that a normal vector of a plane along which the first antenna and/or the second antenna are oriented is aligned essentially parallel to the frontal plane of the patient. The first antenna and the second antenna can flank the patient's jaw region on both sides so as to provide a defined excitation of the tissue of the jaw region between the first antenna and the second antenna by means of the B1 field. In particular, it is conceivable for the first antenna and the second antenna to be disposed in a Helmholtz or Helmholtz-like configuration.

In one embodiment, the transmitter unit comprises at least one third antenna. A signal conductor of the third antenna can have a polygonal or an oval, in particular an elliptical, shape. The third antenna is also preferably disposed planarly in a plane. It is conceivable for a normal vector of the third antenna to be oriented orthogonally to the normal vector of the first antenna and/or the second antenna. In a preferred embodiment, the third antenna is aligned parallel to the frontal plane of the patient and positioned approximately centrally in front of the patient's mouth region. In a predetermined relative position with respect to the patient's jaw region, it is conceivable for the third antenna to be positioned as close as possible to the patient's dentition in order to provide a high level of excitation of the patient's dentition when a radiofrequency signal is applied.

By using a Helmholtz configuration or a Helmholtz-like configuration of the first antenna and the second antenna, a particularly homogeneous B1 field can be advantageously provided in a volume of the patient's jaw region. Thus, the quality of acquired magnetic resonance images of the jaw region of the patient can be advantageously increased.

In another embodiment of the dental coil according to the disclosure, the carrier element is designed to hold the at least one antenna of the transmitter unit in a predetermined relative position with respect to the patient's jaw region, whereby the at least one antenna of the transmitter unit surrounds the outer shape of the jaw region in the predetermined relative position, so that the transmission of radiofrequency signals is essentially limited to a volume of the patient's jaw region.

Similarly to an embodiment described above, the at least one antenna of the transmitter unit can also surround the outer shape of the patient's jaw region in the predetermined relative position. In the predetermined relative position, the at least one antenna of the transmitter unit is preferably shaped conformally to the outer shape of the patient's jaw region in such a way that the excitation of the tissue by means of a radiofrequency signal is essentially limited to a volume of the jaw region, in particular a volume matched to the patient's dentition or to a plurality of teeth. The transmitter unit can be positioned on the carrier element which can be adjusted according to the outer shape of the patient's jaw region e.g. by means of an articulation, a flexible material and/or an adaptation element. However, it is equally conceivable for the transmitter unit to be positioned on a separate retaining element which can be positioned relative to the patient's jaw region. In addition, the dimensions of the transmitter unit, such as the height of the carrier element, the distance between a first antenna and a second antenna, but also a third antenna, and/or an average distance between the transmitter unit and the patient's dentition, can be set in the predetermined relative position of the at least one antenna such that the transmission of radiofrequency signals is essentially limited to the volume of the patient's jaw region. For example, the jaw region volume can include a tooth, a plurality of teeth, a dental arch, a plurality of dental arches, a tooth root, a portion of a jawbone, and/or a portion of a temporomandibular joint.

By limiting the transmission of radiofrequency signals to a volume of the patient's jaw region, the dental coil can be advantageously optimized in respect of an imaging of the patient's dentition. In addition, foldover artifacts in the imaging of the patient's jaw region can be reduced or prevented. A further advantage can be a reduction in costs and space requirements of a dedicated magnetic resonance apparatus for imaging the jaw region compared to conventional magnetic resonance equipment.

In one embodiment of the dental coil according to the disclosure, the transmitter unit comprises at least a first antenna and a second antenna, wherein the first antenna and the second antenna are disposed in an essentially circular and planar manner in parallel-aligned planes separate from one another, such that a projection of a first surface enclosed by the first antenna along a normal vector of the first surface and of a second surface enclosed by the second antenna have a non-empty intersection, wherein the distance corresponds to a height of the patient's jaw region along a longitudinal axis of the patient, and wherein the normal vector of the first antenna is oriented essentially parallel to the longitudinal axis of the patient when the transmitter unit is in a position of use.

As described above, the signal conductor of the first antenna and the signal conductor of the second antenna can be aligned essentially flush with one another. For example, a height of the patient's jaw region can be between 5 and 15 cm. The distance between the first antenna and the second antenna preferably corresponds to at least a distance between a tip of a tooth root of an anterior tooth or canine of the mandible and a tip of a tooth root of an anterior tooth or canine of the maxilla of the patient. In this embodiment, the dental coil can be used in particular for imaging the patient's dentition. However, it is also conceivable for the distance from the first antenna to be larger or smaller, for example, in order to obtain magnetic resonance images of an entire jaw region or only of one dental arch (maxilla or mandible) of the patient. In the position of use, the first antenna and the second antenna are preferably disposed such that the normal vector of the first antenna and/or the second antenna is oriented essentially parallel to the longitudinal axis of the patient. This can mean that, in the position of use, the first antenna and/or the second antenna circumferentially enclose the patient's head along a section of the longitudinal axis of the patient. In particular, the first antenna and the second antenna can be disposed in a Helmholtz configuration or a Helmholtz-like configuration. It is conceivable for the transmitter unit and the receiver unit of the dental coil to be mechanically separate from one another in the position of use on the patient. For this purpose, the transmitter unit can in particular have a retaining element which holds the transmitter unit in a predetermined relative position with respect to the patient's jaw region. It is also conceivable for the retaining element of the transmitter unit to be mechanically connected to the carrier element of the receiver unit and also hold the carrier element in the predetermined relative position with respect to the patient's jaw region.

Providing a separate retaining element for the transmitter unit means that the carrier element with the receiver unit can be positioned on the patient's jaw region independently of the transmitter unit. In addition, with separate positioning of the transmitter unit by means of the retaining element, adjusting a shape of the carrier element to match the patient's jaw region can be advantageously simplified, as it obviates the need to accommodate signal conductors of the transmitter unit in the carrier element.

In another embodiment, the dental coil according to the disclosure has a mount, wherein the mount is designed to hold the carrier element in the position of use on the patient's jaw region, wherein the carrier element and the mount have mutually corresponding plug-in elements which are designed to interconnect the carrier element and the mount in a form-fit manner when they are properly mated.

The mount can be any structure designed to hold the carrier element in the appropriate position of use on the patient's jaw region. In particular, the mount has a plug-in element which, when the mount is properly brought together with the carrier element, engages in a corresponding plug-in element of the carrier element and provides a form-fit connection. It is conceivable for the plug-in element of the carrier element and the plug-in element of the mount to be designed as a bolt and hole or as male and female. Other pairs of plug-in elements which can be geometrically interlocked in any way to provide a form-fit pluggable connection between the carrier element and the mount are of course also conceivable. Preferably, the carrier element and the mount are reversibly interconnected by means of the pluggable connection and can be released from one another by exerting a predetermined force and/or actuating a securing element, such as a securing lever. The mount and the carrier element can each have one or a corresponding plurality of plug-in elements. In a preferred embodiment, the carrier element comprises at least two plug-in elements which can be positioned on opposite sides of a main extent of the carrier element. It is conceivable for the carrier element, when properly mated with the mount, to be moved toward the jaw region along a normal vector of the frontal plane of the patient, wherein the plug-in elements of the carrier element are aligned with the plug-in elements of the mount. The interlocking of the plug-in elements of the carrier element and the plug-in elements of the mount provides a form-fit pluggable connection that holds the carrier element in the predetermined relative position with respect to the patient's jaw region.

In another embodiment, the carrier element is rotatably mounted on a rotatable axis on one side of the patient's head. The carrier element can be guided to the position of use on the patient's jaw region by rotating it about the rotatable axis. On the side of the patient's head opposite the rotatable axis, a mount is preferably provided, having a plug-in element which engages with a corresponding plug-in element of the carrier element in the position of use.

By providing a pluggable connection between the carrier element and the mount, time-efficient positioning of the carrier element on the patient's jaw region can be advantageously provided.

According to one embodiment of the dental coil according to the disclosure, the mount has an electrical connecting cable which is electrically connected to the magnetic resonance apparatus, wherein the plug-in elements are designed to electrically connect the at least one antenna of the transmitter unit and/or the array of antennas of the receiver unit to the electrical connecting cable of the magnetic resonance apparatus.

The carrier element preferably has at least two plug-in elements. The plug-in elements can each have at least two contacts for electrically connecting signal conductors of an antenna, each covering one half of the patient's jaw region. However, fewer plug-in elements or more plug-in elements are also conceivable. As described above, the plug-in elements can be positioned on opposite sides of the main extent of the carrier element. The corresponding plug-in elements of the mount are designed to provide an electrically conductive connection to the signal conductors of the receiver unit when the carrier element is properly mated with the mount. A plug-in element of the carrier element preferably has a male part of a pluggable connection or a female part of a pluggable connection. A corresponding plug-in element of the mount can have a matching counterpart. For example, the plug-in element of the carrier element can have at least one contact pin, while the corresponding plug-in element of the mount can provide at least one corresponding contact hole. The plug-in elements can also comprise pin headers, pin matrices, female connectors and the like, as well as corresponding jacks. It is equally conceivable for the plug-in elements to have both genders (contact pins and contact holes).

The plug-in element or the plurality of plug-in elements of the mount is/are preferably electrically connected to an electrical connecting cable of the magnetic resonance apparatus. For this purpose, contacts of a plug-in element of the mount can be connected to an adapter or directly to the electrical connecting cable. It is conceivable for magnetic resonance signals received by means of the receiver unit to be transmittable from a signal conductor of the array of antennas to the magnetic resonance apparatus via a plug-in element and an electrical connecting cable. It is also conceivable for an alternating current to be transmitted from a radiofrequency unit of the magnetic resonance apparatus to a signal conductor of the transmitter unit by means of an electrical connecting cable and a plug-in element. The transmitter unit is preferably positioned on the carrier element. In a preferred embodiment, the plug-in elements are designed to provide an electrical and mechanical connection between the carrier element and the mount. It is further conceivable for the carrier element and the mount to comprise dedicated plug-in elements for a mechanical connection and dedicated plug-in elements for an electrical connection between the carrier element and the mount.

By providing a plug-in connection for the electrical connection of the carrier element to the mount, it is possible to advantageously provide time-efficient and simple positioning of the carrier element on the patient's jaw region. In addition, free-hanging electrical connecting cables in a facial region of the patient and/or in an image acquisition region of the magnetic resonance apparatus, which can irritate the patient and/or hinder positioning of the carrier element on the patient's jaw region, can be avoided. In addition, the mount of the carrier element can be positioned in a predetermined relative position with respect to the patient's head outside the patient's field of view. As a result, obstruction of the patient's field of view by the carrier element can be advantageously reduced or avoided.

In another embodiment, the local coil according to the disclosure comprises a mount, wherein the mount is designed to hold the carrier element in the position of use on the patient's jaw region, wherein the carrier element comprises an elastic clamping element on a side facing away from the patient, and wherein the mount comprises at least one frame element flanking the head of the patient on both sides along a section of the longitudinal axis of the patient, wherein the carrier element is connected to the mount in the position of use on the patient's jaw region by means of a force-fit connection between the elastic clamping element and the at least one frame element.

In a simple example, the frame element of the mount has two braces oriented approximately parallel to the patient's sagittal plane and flanking at least one section of the patient's head along the longitudinal direction from two sides. The frame element can have a plurality of disjoint parts or be in one piece, wherein, in a one-piece design, the two braces can be connected above or behind the patient's head, for example. A distance between the two braces of the frame element is preferably somewhat less than a width of the carrier element including an elastic clamping element, but at least large enough to allow the patient's head to be positioned between the two braces in a position of use. In the position of use of the carrier element on the patient's jaw region, the carrier element can be positioned between the two braces. An elastic clamping element is preferably positioned on a side of the carrier element facing away from the patient and, in the position of use of the carrier element, rests against the two braces of the mount. The elastic clamping element preferably consists of an elastic foam, e.g. a foam based on polyester, polyurethane or another suitable synthetic or natural material, which is reversibly deformable. Since the distance between the braces can be less than the width of the carrier element comprising the elastic clamping elements, the elastic clamping elements can be compressed between the carrier element and the braces and provide a force-fit connection that holds the carrier element in the position of use. It is conceivable for the frame element to have, on a side facing the carrier element, a profile which supports the force-fit connection between the support and the elastic clamping element.

The carrier element preferably has a plurality of elastic clamping elements positioned on disjoint sub-areas of the carrier element. For example, the carrier element can comprise exactly two elastic clamping elements positioned on opposite sides of the main extent of the carrier element. The elastic clamping elements can be positioned in a lateral orientation on the patient's cheek region and/or temporomandibular joint when the carrier element is positioned for use on the patient. When the carrier element is in the position of use, the patient's mouth region and/or the nose region are preferably clear of an elastic clamping element so as to avoid compromising the patient's breathing.

By providing a force-fit connection between the elastic clamping element and the mount, the carrier element can advantageously be positioned for use on the patient's jaw region in a time-efficient and particularly simple manner. In addition, manufacturing costs for more complex mechanisms for positioning the dental coil can be advantageously reduced or eliminated.

In another embodiment of the dental coil according to the disclosure, the receiver unit has a plurality of antennas which are disposed in rows along an extent of the carrier element, wherein each two adjacent antennas of the receiver unit have an overlap region along the extent of the carrier element, and wherein the overlap region is in the order of 0.5 to 2 cm.

A predetermined overlapping of two adjacent antennas advantageously provides inductive decoupling of the adjacent antennas. This advantageously avoids costs and/or the weight associated with additional electronic components for decoupling the antennas.

According to another embodiment of the dental coil according to the disclosure, in the position of use on the patient's jaw region, the carrier element has a cutout for the patient's nose, wherein at least one antenna of the receiver unit is disposed such that the at least one antenna flanks at least one section of the nose along the longitudinal direction of the patient from one side in order to receive magnetic resonance signals of the root of an anterior tooth of the patient.

A cutout can be an oval or a polygonal notch in the carrier element, the array of antennas of the receiver unit and/or the at least one antenna of the transmitter unit. In particular, the cutout can be designed to provide a clearance for the patient's nose when the carrier element is in the position of use on the patient's jaw region. Contact between the patient's nose and the carrier element can therefore be prevented. The array of antennas of the receiver unit and/or the at least one antenna of the transmitter unit are preferably disposed such that the cutout is clear of signal conductors.

At least one antenna of the receiver unit is disposed such that the at least one antenna flanks at least one section of the nose along the longitudinal direction of the patient on one side. The patient's nose is preferably flanked on two sides when the carrier element is positioned for use, in order to provide adequate coverage of the outer shape of the jaw region with antennas. It is conceivable for the carrier element to have a single antenna or a plurality of antennas, e.g. two or three antennas, in the mouth region and/or nose region of the patient in order to achieve adequate coverage of the outer shape of the patient's jaw region.

The cutout of the carrier element advantageously enables interference with the patient's breathing to be reduced or prevented when the carrier element is in the position of use. In addition, the cutout can advantageously have a positive effect on the comfort of the patient during magnetic resonance imaging.

In one embodiment, the dental coil according to the disclosure comprises a mount and a bite bar, wherein the mount is designed to hold the carrier element in the position of use on the patient's jaw region and wherein the bite bar is mechanically connected to the mount and is designed to align the patient's jaw region in a predetermined relative position with respect to the carrier element when the bite bar is properly positioned on the patient's dentition.

When properly positioned on the patient's dentition, the bite bar is preferably positioned between the patient's maxilla and mandible. The shape of the bite bar can approximate to the shape of a patient's dental arch. The bite bar preferably has a circumferential recess which is designed to accommodate the patient's dental arch. This allows the bite bar to be correctly positioned on the dentition when the maxilla and mandible are brought together. It is conceivable for the bite bar to be guided to the patient's maxilla by the mount in order to fix the patient's maxilla. The mount can have a suitable adjustment mechanism for this purpose, which enables the position of the bite bar in relation to the patient's dentition, the carrier element and/or the mount to be adjusted. In one embodiment, the bite bar is designed to fix the patient's maxilla while the patient's mandible remains movable for dynamic imaging of the temporomandibular joint.

A bite bar material preferably has high biocompatibility. A material with high biocompatibility is characterized in particular by high cell and blood compatibility and is preferably histopathologically unproblematic. Possible materials are, for example, plastics such as silicones, polyethers, polyamides, polycarbonates, but also polymers of various natural substances such as proteins, saccharides, peptides and the like. In addition, ceramics such as aluminum oxide, gypsum, hydroxyapatite and the like are also conceivable.

The bite bar can be mechanically connected to the mount using any fastening means. In particular, the bite bar is connected to the mount in a predetermined relative position with respect to the carrier element. In one embodiment, the bite bar can be mechanically connected to the carrier element by means of the mount. The dimensions and/or a shape of the mount can be selected such that the carrier element is guided into a position of use on the patient's jaw region when the bite bar is properly positioned on the patient's dentition. In a preferred embodiment, the bite bar is detachably connected to the mount so that the bite bar can be replaced or cleaned separately from the mount.

Providing the bite bar enables relative movement of the patient's jaw region with respect to the carrier element to be limited. This advantageously reduces or prevents the occurrence of image artifacts caused by patient movement during magnetic resonance imaging.

In one embodiment, the dental coil according to the disclosure has a mount and an adjustment mechanism, wherein the mount is designed to hold the carrier element in the position of use on the patient's jaw region, and wherein the adjustment mechanism is designed to position the carrier element relative to the patient's jaw region.

It is conceivable for the carrier element to be mechanically connected to a mount that holds the carrier element in the position of use on the patient's jaw region. The mount can, for example, be mechanically connected to the magnetic resonance apparatus or be a separate component. The mount can be designed to move the carrier element of the dental coil towards the patient along at least one predetermined direction depending on the patient's positioning, e.g. recumbent, sitting or standing. The at least one predetermined direction is preferably oriented parallel to the sagittal plane of the patient. It is also conceivable for the mount to comprise further components for supporting and/or fixing the head of the patient. For example, the mount can comprise a chin rest, a bite bar, a head shell, a head rest, a frame, or the like, which limit head movement in at least one spatial direction, preferably in a plurality of spatial directions. In one embodiment, the mount is of multi-part design, wherein the components of the mount can be positioned independently of one another and/or independently of the carrier element of the dental coil. The components of the mount can conceivably be adapted to suit the position and/or shape of the patient's head before the carrier element is connected to the mount.

Providing the mount and adjustment mechanism advantageously enables the carrier element to be positioned precisely and repeatably in the position of use on the patient's jaw region.

The magnetic resonance system according to the disclosure comprises a magnetic resonance apparatus and a dental coil according to an abovementioned embodiment, wherein the magnetic resonance apparatus is designed to detect magnetic resonance signals of a patient's jaw region by means of the dental coil.

The magnetic resonance apparatus can comprise a mount designed to hold at least part of the dental coil, such as a carrier element, a receiver unit and/or a transmitter unit, in a predetermined position relative to a patient's jaw region. For this purpose, the mount can be mechanically connected to the magnetic resonance apparatus, in particular a patient positioning device or a patient table. However, it is conceivable for the mount to be a separate component from the magnetic resonance apparatus. In this case, the mount can be mounted on a wall and/or roof of an examination space of the magnetic resonance apparatus or can be connected to the patient table. The mount preferably comprises at least one adjustment mechanism designed to adjust a position of the mount and/or of at least part of the dental coil relative to the patient positioning device and/or the patient. In particular, it is conceivable for the adjustment mechanism to be designed to adjust a spatial position of the at least one part of the dental coil and/or of the mount.

In addition, the magnetic resonance system according to the disclosure comprises at least one electrical connecting cable which is designed to electrically connect the dental coil to the magnetic resonance apparatus. In one embodiment, the transmitter unit of the dental coil is connected to a radiofrequency unit of the magnetic resonance apparatus by means of an electrical connecting cable. The radiofrequency unit can provide an alternating current which is transmitted as a radiofrequency signal from the transmitter unit into a volume of the patient's jaw region and produces a B1 magnetic field. In another embodiment, the receiver unit of the dental coil is connected to a receiver channel of the magnetic resonance apparatus by means of an electrical connecting cable. The magnetic resonance apparatus is thus able to receive magnetic resonance signals of the patient's jaw region and to produce magnetic resonance images in response to the magnetic resonance signals received.

The magnetic resonance system according to the disclosure can advantageously enable magnetic resonance images of the patient's jaw region to be acquired in a time-efficient and repeatable manner. In addition, a quality of magnetic resonance images of the patient's jaw region can advantageously be increased by precise and repeatable positioning of the dental coil on the patient's jaw region by means of the mount.

BRIEF DESCRIPTION OF THE DRAWINGS

Further advantages and details will emerge from the following description of exemplary embodiments with reference to the accompanying drawings in which.

DETAILED DESCRIPTION OF THE DISCLOSURE

Figure 1:
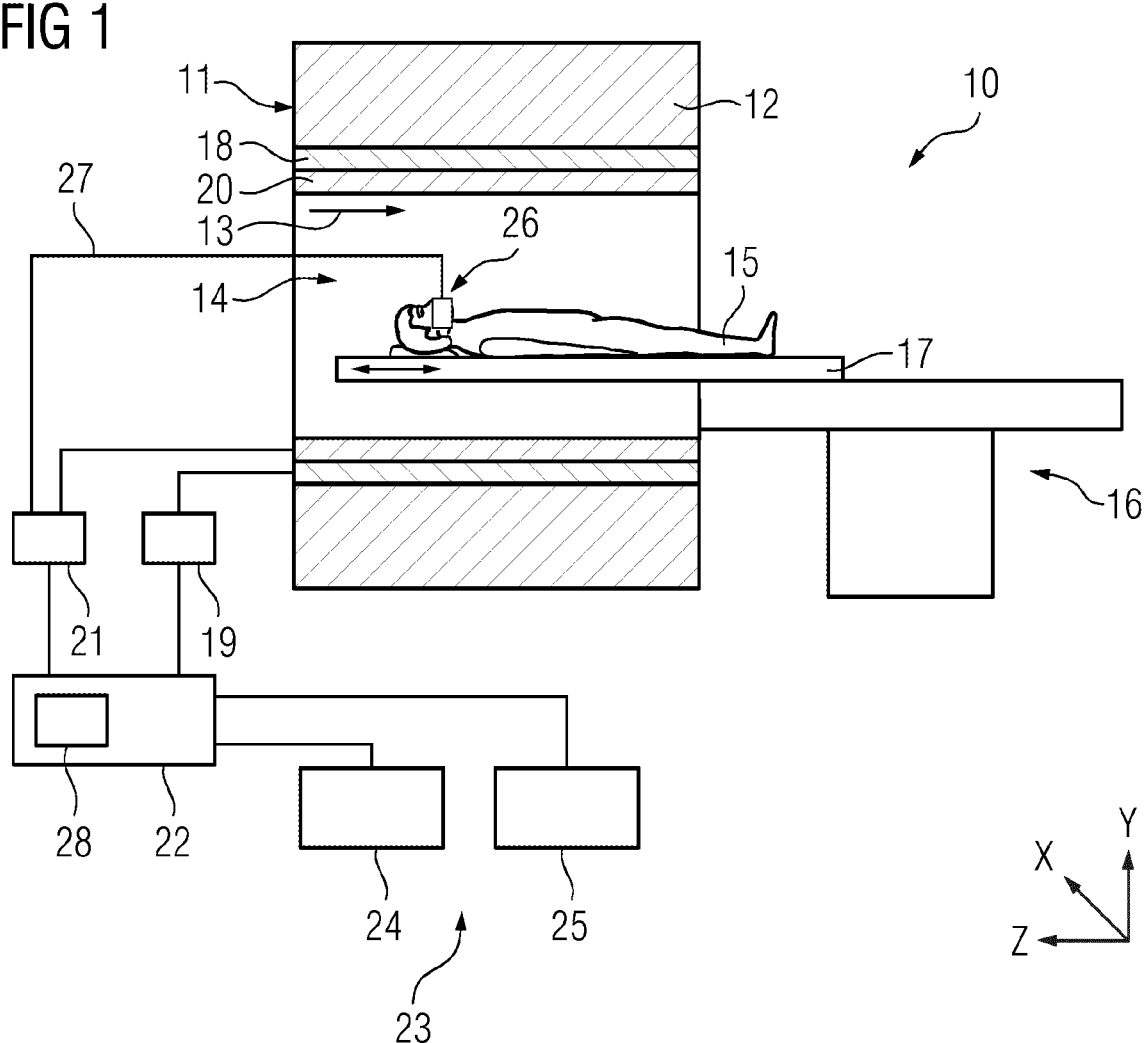
FIG. 1 shows a possible embodiment of a magnetic resonance system according to the disclosure.

FIG. 1 schematically illustrates a possible embodiment of a magnetic resonance system 1 comprising a magnetic resonance apparatus 10 and a dental coil 26. The magnetic resonance apparatus 10 has a magnet unit 11 comprising e.g. a permanent magnet, an electromagnet or a superconducting main magnet 12 for generating a powerful and, in particular, homogeneous main magnetic field 13 (B0 field). In addition, the magnetic resonance apparatus 10 comprises a patient receiving area 14 for accommodating a patient 15. In this exemplary embodiment, the patient receiving area 14 is cylindrical in shape and is circumferentially enclosed by the magnet unit 11. In principle, however, configurations of the patient receiving area 14 that differ from this example are also conceivable.

The patient 15 can be positioned in the patient receiving area 14 by means of a patient positioning device 16 of the magnetic resonance apparatus 10. For this purpose, the patient positioning device 16 comprises a patient table 17 which is designed to be movable within the patient receiving area 14. In addition, the magnet unit 11 comprises a gradient coil 18 for generating magnetic gradient fields which are used for spatial encoding during an MRI scan. The gradient coil 18 is controlled by means of a gradient control unit 19 of the magnetic resonance apparatus 10. The magnet unit 11 can also comprise a radiofrequency antenna which in this exemplary embodiment is implemented as a body coil 20 permanently incorporated into the magnetic resonance apparatus 10. The body coil 20 is designed to excite atomic nuclei present in the main magnetic field 13 generated by the main magnet 12. The body coil 20 is controlled by a radiofrequency unit 21 of the magnetic resonance apparatus 10 and injects radiofrequency signals into an examination space essentially formed by a patient receiving area 14 of the magnetic resonance apparatus 10. The body coil 20 can be additionally designed to receive magnetic resonance signals.

The magnetic resonance apparatus 10 has a control unit 22 for controlling the main magnet 12, gradient control unit 19 and radiofrequency unit 21. The control unit 22 is designed to control the execution of a sequence, such as an imaging gradient echo sequence, a TSE sequence or a UTE sequence. The control unit 22 also comprises an evaluation unit 28 for analyzing digitized magnetic resonance signals acquired during magnetic resonance imaging. The evaluation unit can also be designed to use reconstruction methods to reconstruct image data from reduced sets of k-space data when using parallel imaging techniques.

In addition, the magnetic resonance apparatus 10 comprises a user interface 23 having a signal connection to the control unit 22. Control information such as imaging parameters and reconstructed magnetic resonance images can be displayed to a user on a display unit 24, e.g. on at least one monitor, of the user interface 23. In addition, the user interface 23 comprises an input unit 25 by means of which magnetic resonance imaging parameters can be entered by the user. The magnetic resonance apparatus 10 also comprises a dental coil 26 which is positioned on the jaw region 43 of a patient 15 (see FIG. 2) and transfers magnetic resonance signals from a volume of the jaw region 43 to the magnetic resonance apparatus 10. The dental coil 26 preferably has an electrical connecting cable 27 that provides a signal connection to the radiofrequency unit 21 and the control unit 22. Like the body coil 20, the dental coil 26 can also be designed to excite atomic nuclei and receive magnetic resonance signals. A transmitter unit of the dental coil 26 is triggered by the radiofrequency unit 21 to emit radiofrequency signals. The dental coil 26 can have a drum-shaped structure (see FIG. 7), for example, which circumferentially encloses the head of the patient 15 along the patient's longitudinal extent. However, the transmitter unit and the receiver unit of the dental coil 26 can also be connected to a carrier element 30 which is adjusted to suit the outer shape of the patient's jaw region and is positioned on the jaw region 43 of the patient 15 (see FIG. 6).

The magnetic resonance apparatus 10 shown can obviously comprise further components usually found in magnetic resonance equipment. It is also conceivable for the magnetic resonance apparatus 10 to have a C-shaped, triangular or asymmetrical structure of the magnetic-field-generating components instead of the cylinder-shaped structure. In particular, the magnetic resonance apparatus 10 can be a dedicated magnetic resonance apparatus 10 designed to perform magnetic resonance imaging of the jaw region of a standing or seated patient 15.

Figure 2:
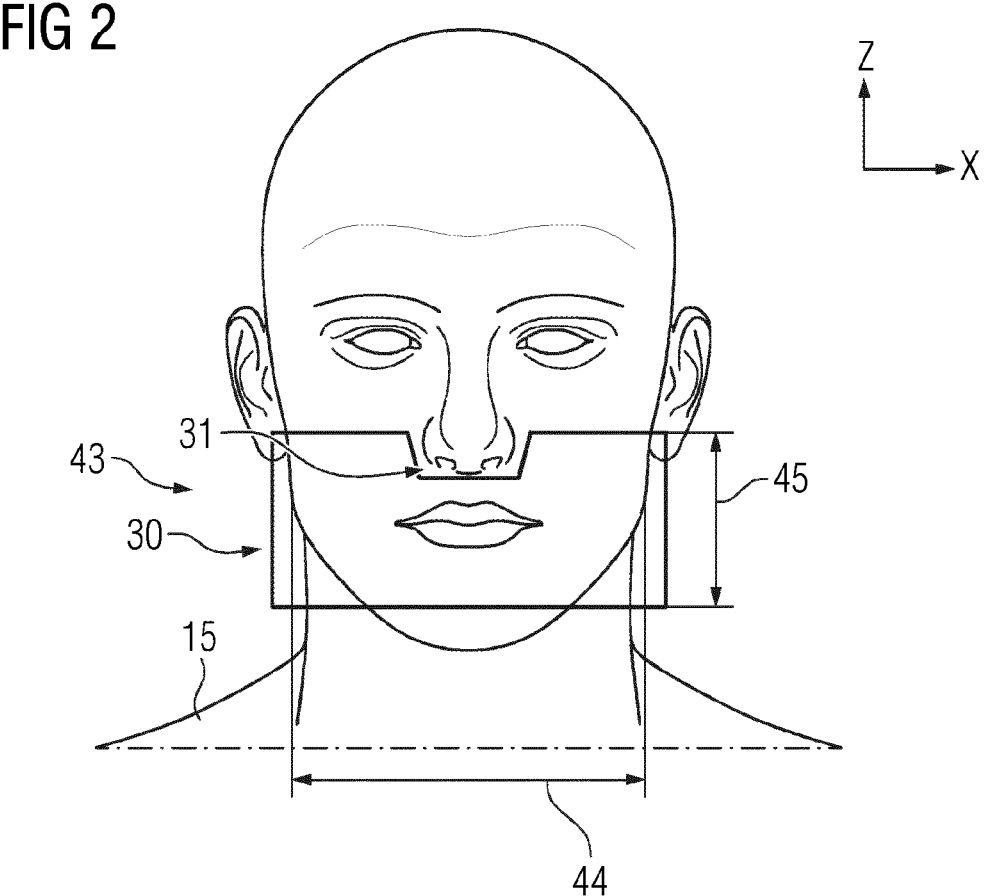
FIG. 2 shows a possible embodiment of a carrier element of a dental coil according to the disclosure.

FIG. 2 shows a frontal view of the patient 15 with a carrier element 30 of the dental coil 26 according to the disclosure. The carrier element 30 is positioned in the position of use on the jaw region 43 of the patient 15 and frames the jaw region 43 of the patient 15 across the width of the jaw region 44 and the height of the jaw region 45. The carrier element 30 further comprises a cutout 31 which provides a clearance for the nasal region of the patient 15 and facilitates breathing of the patient 15. The carrier element 30 can also have a horseshoe-shaped cross-section that corresponds to the outer contour of the jaw region 43 of the patient 15. The carrier element 30 is preferably positioned at a short distance of between one millimeter and five millimeters from the jaw region 43 of the patient 15.

Figure 3:
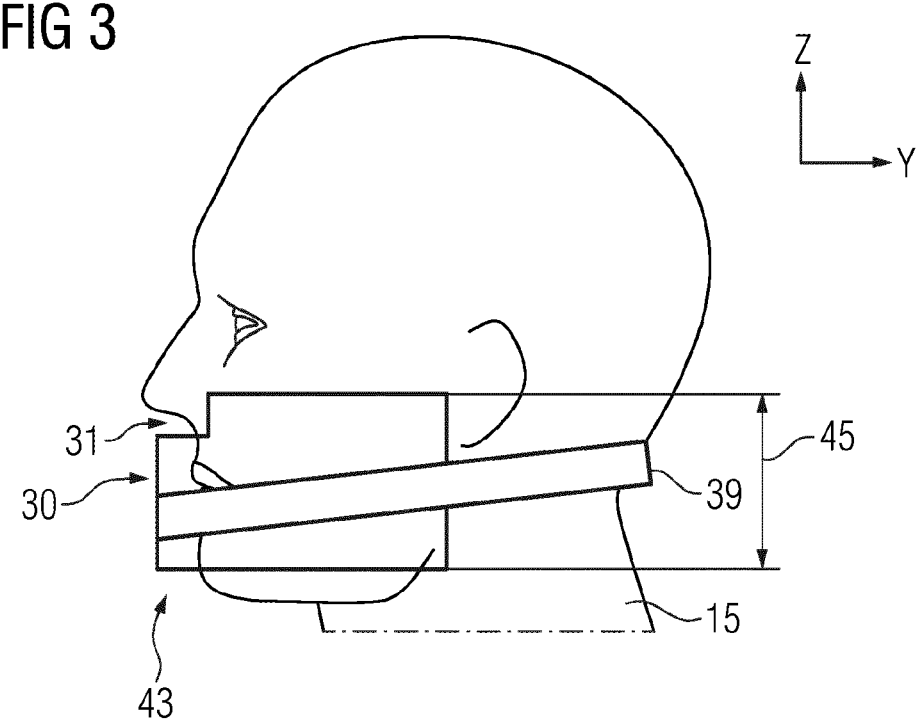
FIG. 3 shows a possible embodiment of a carrier element of a dental coil according to the disclosure.

FIG. 3 shows a side view of a patient 15 with a carrier element 30 in the position of use on the jaw region of the patient 15. The carrier element 30 encloses the jaw region 43 of the patient 15 and covers at least a part of the temporomandibular joint of the patient 15. It is conceivable for the carrier element 30 to also enclose the base of the ear of the patient 15 so that magnetic resonance signals of the temporomandibular joint of the patient 15 can be acquired. It is likewise conceivable for the carrier element 30 to also enclose the chin and/or cheekbones of the patient 15 in order to receive magnetic resonance signals from these regions.

In the example shown, the carrier element 30 comprises a flexible material that is shaped to match the jaw region 43 of the patient 15 by means of an adaptation element 39. In this embodiment, the adaptation element 39 comprises a tensioning strap that circumferentially surrounds the jaw region 43 and the carrier element 30 and can be adjusted according to the circumference of the jaw region 43 of the patient 15. When the tensioning strap is tightened, the carrier element 30 is fixed in the position of use on the jaw region 43 of the patient 15, wherein the array of antennas 32 of the receiver unit (see FIG. 4) is shaped according to the jaw region 43 of the patient 15. Further mechanisms that are designed to adjust the carrier element 30 to match the jaw region 43 of the patient 15 are self-evidently also conceivable. In particular, it is conceivable for the adaptation element 39 to have a frame or be connected to a mount 35 (see FIG. 9) so as to avoid contact between the carrier element 30 and the skin surface of the patient 15 when adjusting the bending radius of the carrier element 30.

Figure 4:
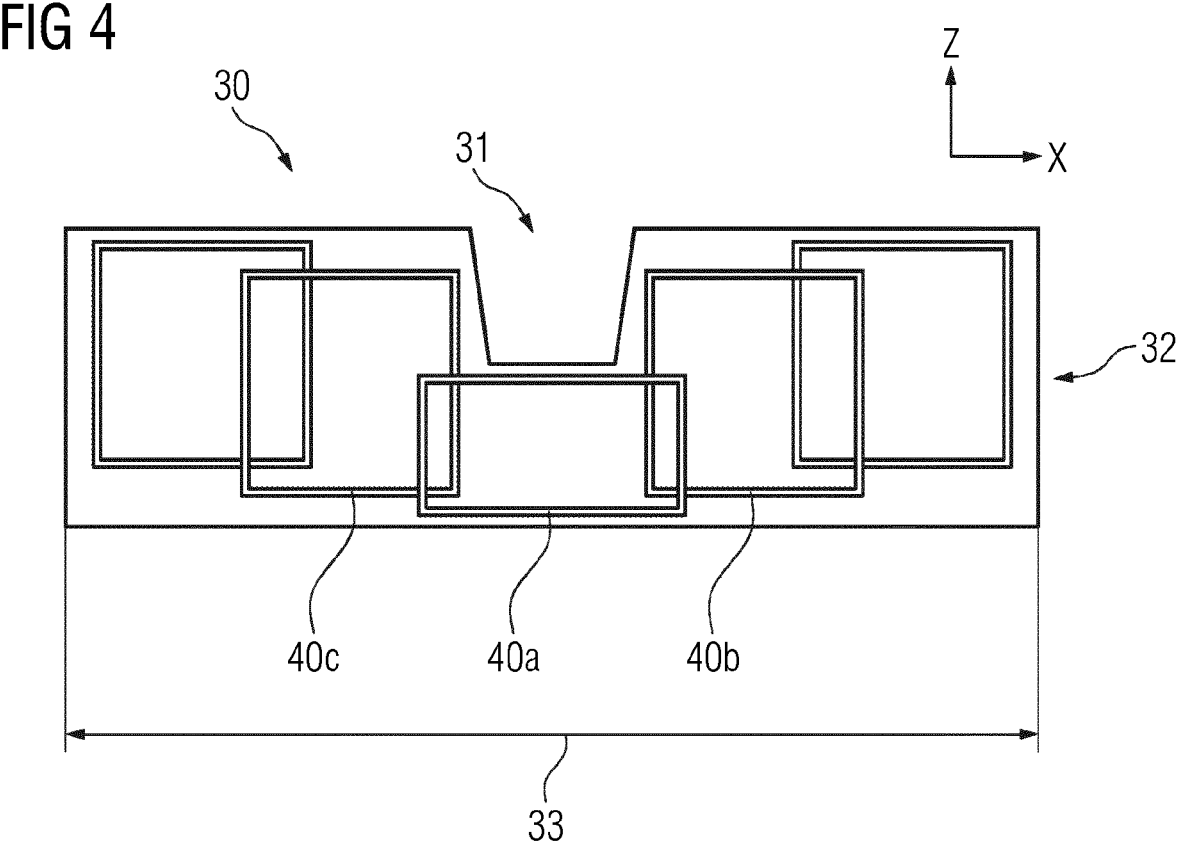
FIG. 4 shows a possible embodiment of a receiver unit of a dental coil according to the disclosure.

FIG. 4 shows an array of antennas 32 of a receiver unit of the dental coil 26 according to the disclosure. In the example shown, the carrier element 30 is spread out planarly along the main extent 33, resulting in an essentially rectangular shape. The carrier element 30 can be made of a flexible material or have segments of a flexible material, such that the carrier element 30 can be molded to the jaw region 43 of the patient 15 from the planar shape shown. In the example shown, the carrier element 30 has an array of antennas 32 which are disposed in series with one another, partially overlapping along the main extent 33 of the carrier element 30. Every two adjacent antennas 40a and 40b can have an overlap region 0.5 to 2 cm wide in the X direction. In addition, it is conceivable for the carrier element 30 to have a compensation mechanism (not shown) that adjusts an overlap region between the two adjacent antennas 40a and 40b when the carrier element 30 is deformed. The overlap region enables the two antennas 40a and 40b to be inductively decoupled from one another.

The antennas of the receiver unit are disposed in the carrier element 30 in such a way that there are no signal conductors or antennas 40 in the area of the cutout 31. The nose region of the patient 15 (not shown) is flanked laterally by the antennas 40b and 40c. The antennas 40b and 40c can extend along the Z-direction at least to the extent that magnetic resonance signals can be received from tips of dental roots of the incisors and/or canines of the maxilla and/or mandible of the patient 15.

The array of antennas 32 can be embedded in the material of the carrier element 30 and/or form-fitted, force-fitted and/or integrally bonded to the carrier element 30. The array of antennas 32 preferably has between four and ten antennas 40. As well as an odd number of antennas 40, whereby the antenna 40a is preferably positioned centrally on the sagittal plane of the patient 15, the array of antennas 32 can also have an even number of antennas 40.

Figure 5:
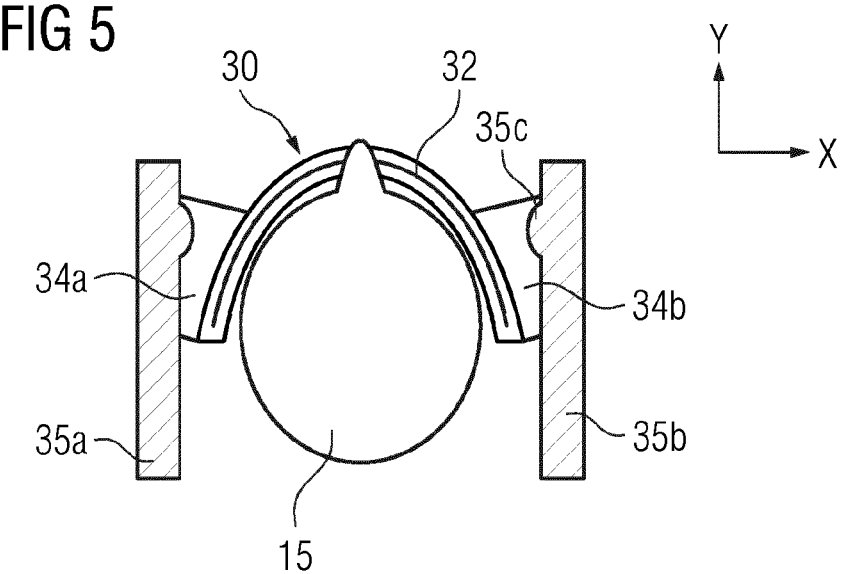
FIG. 5 shows a possible embodiment of a dental coil according to the disclosure.

FIG. 5 shows an embodiment of the dental coil 26 according to the disclosure in which the carrier element 30 has an elastic clamping element 34 which holds the carrier element 30 in the position of use on the jaw region 43 of the patient 15 by means of a force-fit connection with two braces 35a and 35b of a frame element of the mount 35. In the example shown, the dental coil 26 has two elastic clamping elements 34a and 34b positioned laterally on opposite sides of the main extent 33 of the carrier element 30. The elastic clamping elements are positioned on the side of the carrier element 30 facing away from the patient 15 and are compressed between the two braces 35a and 35b when the carrier element 30 is appropriately positioned for use on the jaw region 43 of the patient 15. The two braces 35a and 35b can have a profiling, such as a roughened surface and/or a continuous protrusion 35c in the Z-direction, which supports the force-fit connection between the two braces 35a and 35b of the mount 35 and the clamping elements 34a and 34b.

In the example shown, in the predetermined relative position with respect to the jaw region 43, the array of antennas 32 of the receiver unit is shaped to conform to the outer contour of the jaw region 43 of the patient 15. In said predetermined relative position, the array of antennas 32 is preferably spaced approximately one to five millimeters from the skin surface of the patient 15.

Figure 6:
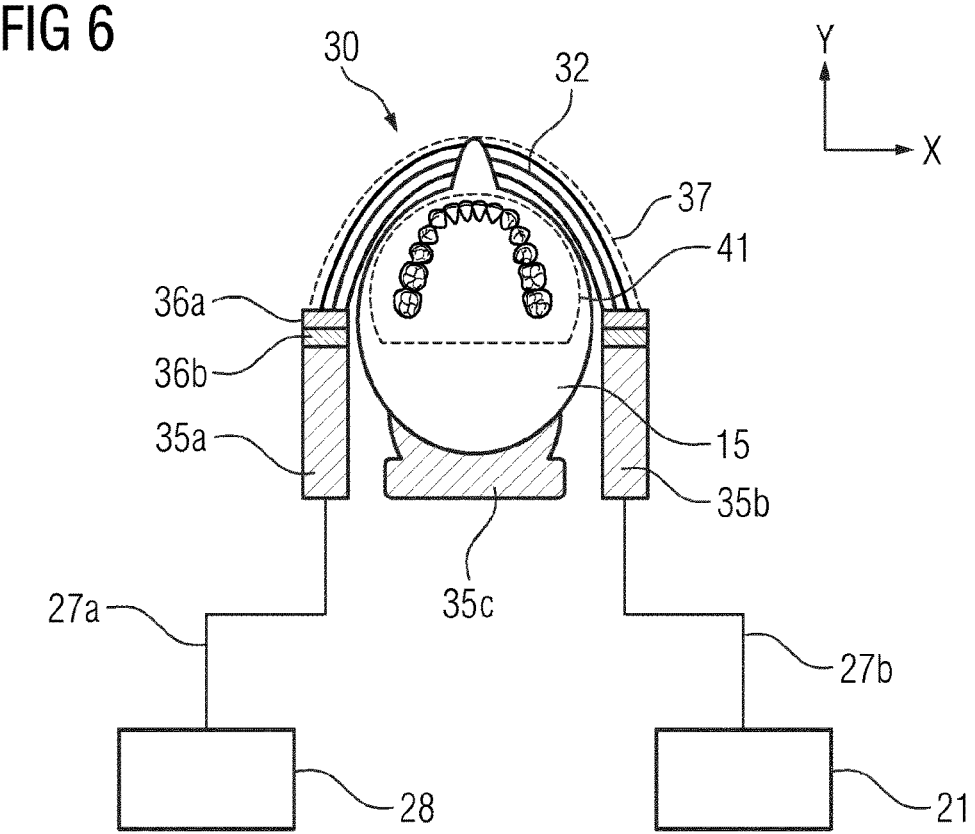
FIG. 6 shows a possible embodiment of a dental coil according to the disclosure.

FIG. 6 shows an embodiment of the dental coil 26 according to the disclosure in which the carrier element 30 has a plug-in element 36a which holds the carrier element 30 in the position of use on the jaw region 43 of the patient 15 by means of a form-fitting connection with a plug-in element 36b of the mount 35. The plug-in element 36a of the carrier element 30 and the plug-in element 36b of the mount 35 engage with each other when the carrier element 30 and the mount 35 are properly brought together, thereby preventing involuntary displacement or shifting of the carrier element 30 caused by movement of the patient 15. The plug-in elements 36a and 36b can also provide an electrical connection of the array of antennas 32 of the receiver unit and/or of the at least one antenna 37 of the transmitter unit to an electrical connecting cable 27. In the example shown, received magnetic resonance signals of the array of antennas 32 of the receiver unit are transmitted to the evaluation unit 28 of the magnetic resonance apparatus 10 by means of the electrical connecting cable 27a. The evaluation unit 28 can then reconstruct a magnetic resonance image from the received magnetic resonance signals. In addition, an alternating current is transmitted by means of the electrical connecting cable 27b from the radiofrequency unit 21 via the plug-in elements 36a and 36b to the at least one antenna 37 of the transmitter unit which then transmits a radiofrequency signal into the jaw region 43 of the patient 15. In the example shown, the electrical connecting cables 27a and 27b are connected to opposite sides of the mount 35 for the sake of clarity. Self-evidently, the array of antennas 32 and the at least one antenna 37 can be connected to the electrical connecting cables 27a and 27b by means of separate or common plug-in connections (36a, 36b) and/or at any positions on the dental coil 26.

In this example, the mount 35 has a plurality of mechanically separate components. In addition to the two braces 35a and 35b that have the plug-in elements 36b, the mount 35 also comprises a head shell 35c that restricts movement of the head of the patient 15 during magnetic resonance imaging.

In this embodiment, the transmission of radiofrequency signals by means of at least one antenna 37 of the transmitter unit is approximately limited to a volume 41 of the jaw region 43 (shown here schematically in a two-dimensional view). This can ensure that other anatomical regions of the patient 15 cannot be examined by means of the dental coil 26. This may be relevant for dental clinics and practices that cannot or are not allowed to perform diagnostics outside the usual anatomy areas for dentistry. Depending on the embodiment of the dental coil 26 and individual adjustment of the dental coil 26 to suit the jaw region 43 of the patient 15, the shape and/or dimension of the volume 41 of the jaw region 43 that can be magnetized by means of the transmitter unit can obviously differ from the example shown in FIG. 6 which is to be understood as schematic.

Figure 7:
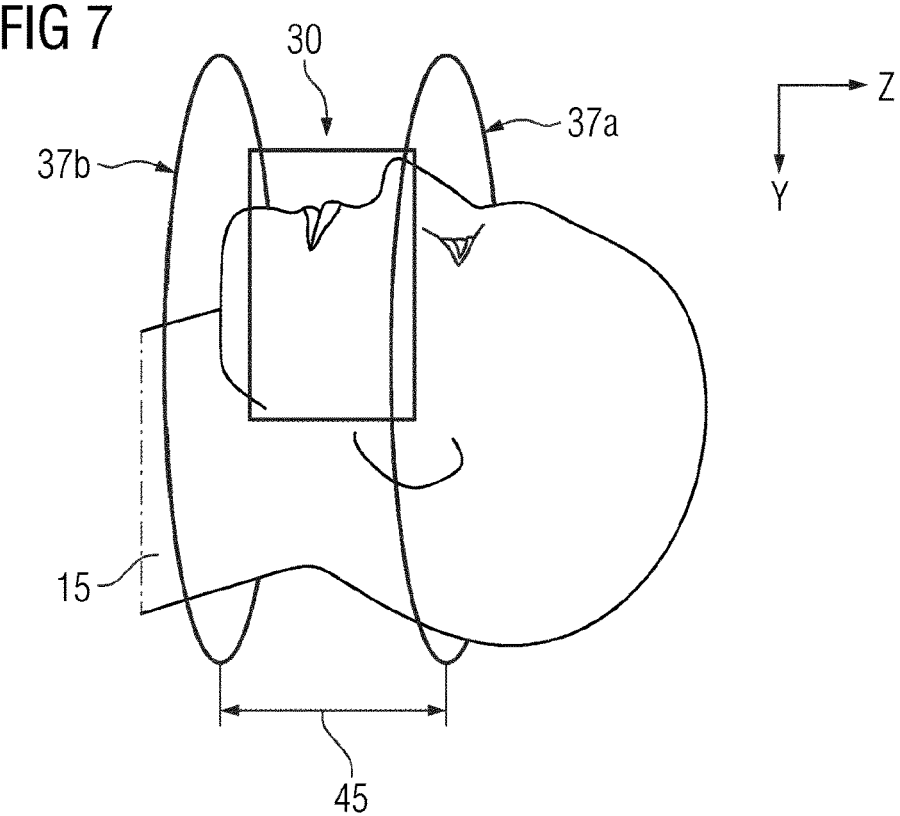
FIG. 7 shows a possible embodiment of a transmitter unit of a dental coil according to the disclosure.

FIG. 7 shows an embodiment of the dental coil 26 in which the transmitter unit comprises a first antenna 37a and a second antenna 37b. The first antenna 37a and the second antenna 37b have an essentially planar extent and are aligned parallel to one another, offset by a distance. The distance between the first antenna 37a and the second antenna 37b corresponds to the height of the jaw region 45 of the patient 15 along the Z-direction. The transmitter unit is designed such that the first antenna 37a and the second antenna 37b circumferentially surround at least part of the head of the patient 15 along the Z-direction. A normal vector of the first antenna 37a is oriented essentially parallel to the longitudinal axis of the patient 15 (Z-direction) in the position of use of the transmitter unit. The transmitter unit can, for example, comprise a drum-shaped retaining element (not shown) which holds the first antenna 37a and the second antenna 37b in a predetermined relative position with respect to one another. It is equally conceivable for the carrier element 30 also to be held in the position of use by the retaining element. The retaining element can in particular be a mount 35 or a component of the mount 35.

Figure 8:
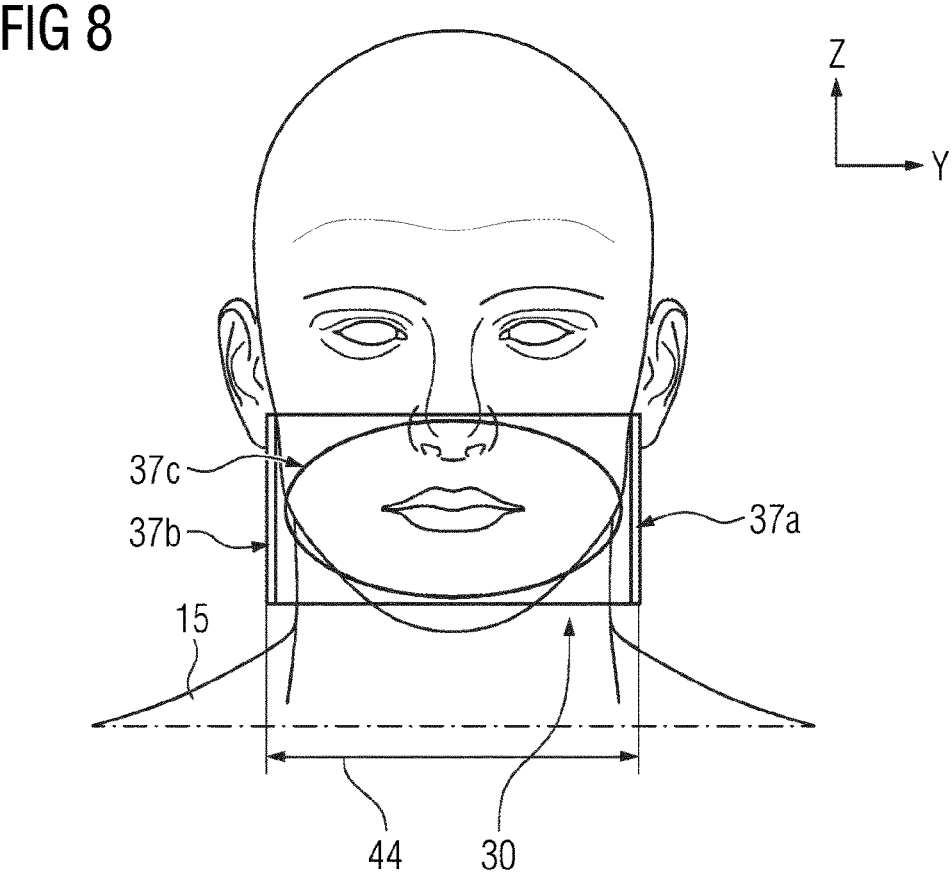
FIG. 8 shows a possible embodiment of a transmitter unit of a dental coil according to the disclosure.

FIG. 8 shows an embodiment of the dental coil 26 according to the disclosure in which the distance between the first antenna 37a and the second antenna 37b approximately corresponds to the width of the jaw region 44 of the patient 15 and in which the normal vector of the first antenna 37a is oriented essentially parallel to the X-direction. The first antenna 37a and the second antenna 37b are preferably circular in shape and flank the jaw region 43 of the patient 15 on the cheek regions from two sides. In this embodiment, the first antenna 37a and the second antenna 37b of the transmitter unit are positioned on the carrier element 30 which according to an embodiment described above is designed to hold the transmitter unit in a predetermined relative position with respect to the jaw region 43 of the patient 15.

The transmitter unit can additionally comprise a third antenna 37c which has a planar extent and is positioned essentially parallel to the frontal plane of the patient 15 in a central position in front of the mouth region of the patient 15. In the example shown, the third antenna 37c has an elliptical shape to provide a high degree of coverage of the jaw region 43 of the patient 15. However, it is equally conceivable for the third antenna 37c to have an oval or polygonal shape. By adapting the transmitter unit to suit the jaw region 43 of the patient 15, in particular by adapting the distance between the first antenna 37a and the second antenna 37b to match the width of the jaw region 44 as well as a diameter of the first antenna 37a and the second antenna 37b to match the height of the jaw region 45, the excitation of the tissue of the patient 15 by means of the transmitter unit can be limited to a volume of the jaw region 43.

In particular, the embodiments of the transmitter unit shown in FIG. 7 and FIG. 8 can have a Helmholtz configuration or a Helmholtz-like configuration in respect of the first antenna 37a and the second antenna 37b.

Figure 9:
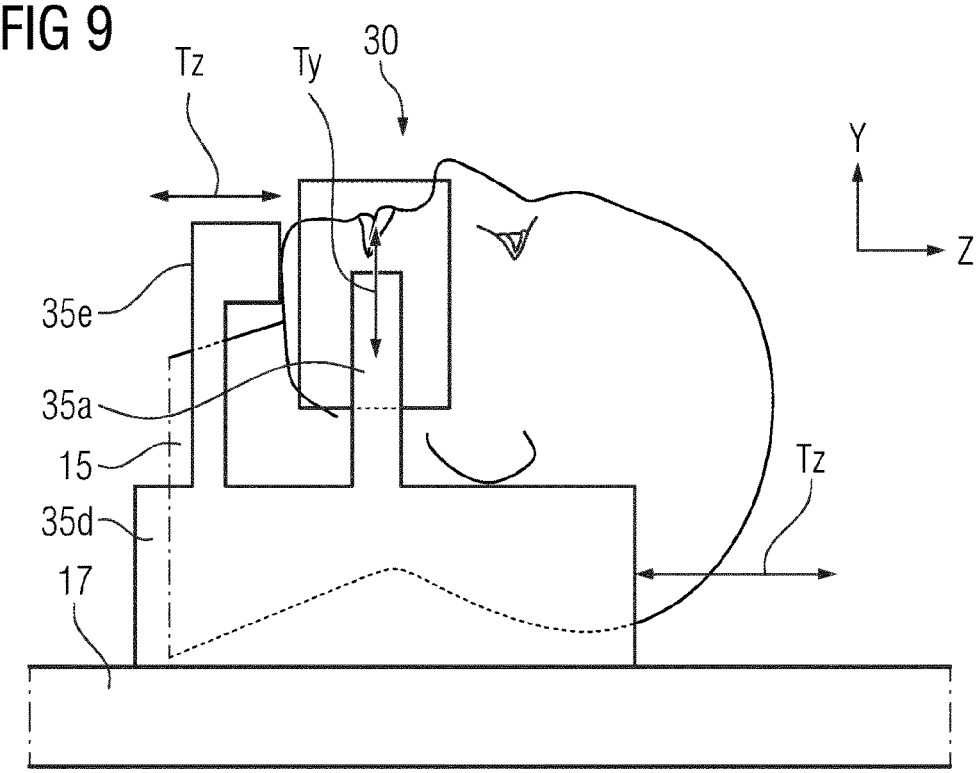
FIG. 9 shows a possible embodiment of a mount of a dental coil according to the disclosure.

FIG. 9 shows an embodiment of the dental coil 26 according to the disclosure in which the mount 35 comprises a plurality of components. In the example shown, the patient 15 is recumbent on the patient table 17 so that the head of the patient 15 is positioned in the predetermined relative position with respect to a head rest 35d. The head rest can have a frame structure, a neck support, head support or the like designed to accommodate and/or stabilize the head of the patient 15. The mount 35 has braces 35a and 35b (not shown) which hold the carrier element 35 in the position of use on the jaw region 43 of the patient 15. For this purpose, the carrier element 30 can be connected to the braces 35a and 35b e.g. by means of a plug-type connection (36a, 36b). In addition, the mount 35 can have an adjustment mechanism (not shown) which is designed to adjust the position of the carrier element 30 at least along the path Ty in the Y-direction. It is also conceivable for the two braces 35a and 35b to comprise an adaptation element 39 (not shown) which is designed to deform the carrier element 30 along the X-direction and thus adapt the bending radius of the carrier element 30 to match the shape of the jaw region 43 of the patient 15. The two braces 35a and 35b, or parts of the two braces 35a and 35b, can be positionable along the X-direction for this purpose.

The mount 35 further comprises a chin support 35e, the position of which is adjustable at least along the path Tz in the Z-direction. In the position of use, the chin support can be guided in the Z-direction against the chin of the patient 15 in order to limit movement of the mandible of the patient 15 during magnetic resonance imaging. It is also conceivable that the head rest 35d can be positioned on the patient table 17 at least along the path Tz by means of a guide mechanism (not shown).

Figure 10:
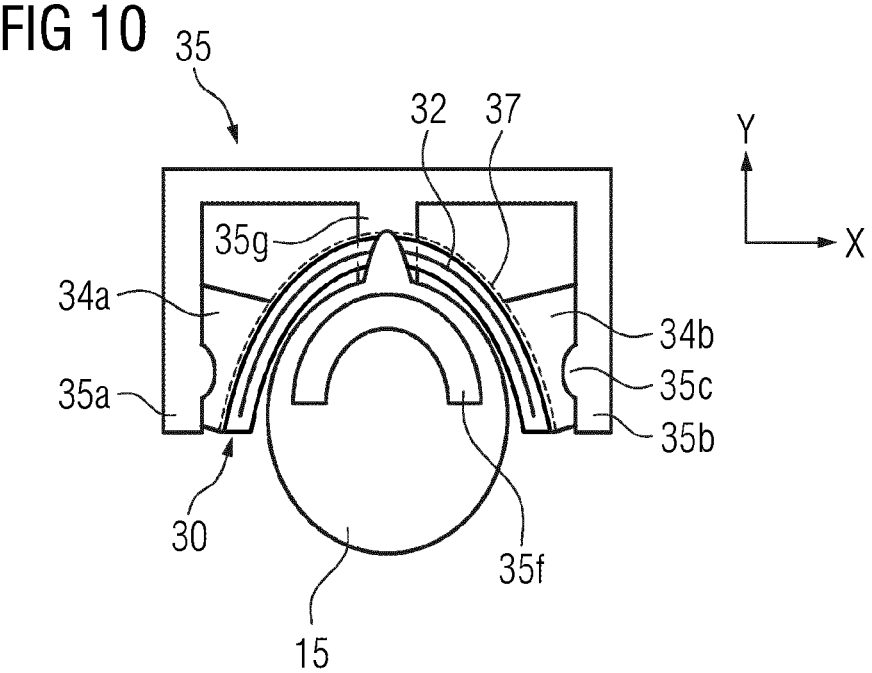
FIG. 10 shows a possible embodiment of a dental coil according to the disclosure.

FIG. 10 shows another embodiment of the dental coil 26 according to the disclosure in which the carrier element 30 is connected in a force-fit manner to two braces 35a and 35b of the mount 35 by means of two elastic clamping elements 34a and 34b. In this embodiment, the mount 35 additionally comprises a bite bar 35f which is mechanically connected to the mount 35 by means of a holding arm 35g. In the position of use, the bite bar 35f is positioned at least on the maxilla of the patient 15 so that movement of the jaw region 43 of the patient 15 during magnetic resonance imaging is limited or prevented. A position of the carrier element 30 can preferably be adjusted along the Z-direction and the Y-direction while the maxilla of the patient 15 is connected to the bite bar 35f. The position of the carrier element 30 can be adjusted e g manually or automatically by overcoming frictional forces between the elastic clamping elements 34a and 34b and the braces 35a and 35b.

Figure 11:
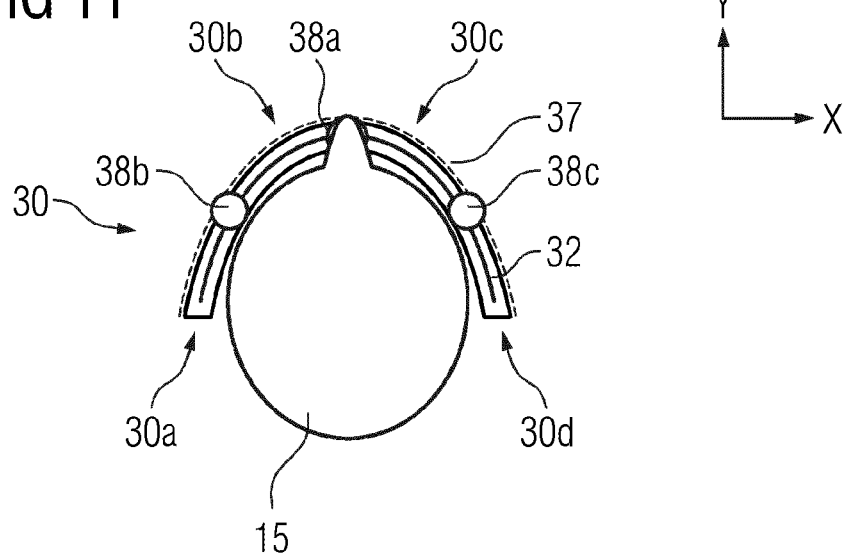
FIG. 11 shows a possible embodiment of a carrier element of a dental coil according to the disclosure.

FIG. 11 shows an embodiment of the dental coil 26 in which the carrier element 30 has articulations 38a, 38b, and 38c (38a-c) for adapting a shape of the carrier element 30 to the jaw region 43 of the patient 15. The articulations 30a-c divide the carrier element 30 into four segments 30a, 30b, 30c, and 30d (30a-d) which are disposed around the jaw region 43 of the patient 15. The articulations 38a-c are designed to adjust angles between the segments 30a-d. The individual segments 30a-d can thus be disposed at a desired spacing and/or with a desired orientation with respect to the jaw region 43 of the patient 15. The articulations 38a-c can be oriented along the Z-direction so that the carrier element 30 is divided into approximately vertical segments 30a-d, as shown in FIG. 11. However, it is equally conceivable for the articulations 38a-c to be disposed at an angle to the Z-direction so that the carrier element 30 can be better adjusted to the anatomical requirements of the jaw region 43 of the patient 15.

As shown in FIGS. 6, 8, 10 and 11, the at least one antenna of the transmitter unit can surround the outer shape of the jaw region 43 of the patient 15 in the predetermined relative position such that the transmission of radiofrequency signals is essentially limited to a volume of the jaw region 43 of the patient 15. In the embodiment of the dental coil 26 shown in FIG. 7, neck region tissue of the patient 15 at the level of the jaw region 43 is additionally excited, which can be advantageous for comprehensive imaging of the temporomandibular joints of the patient 15.

Figure 12:
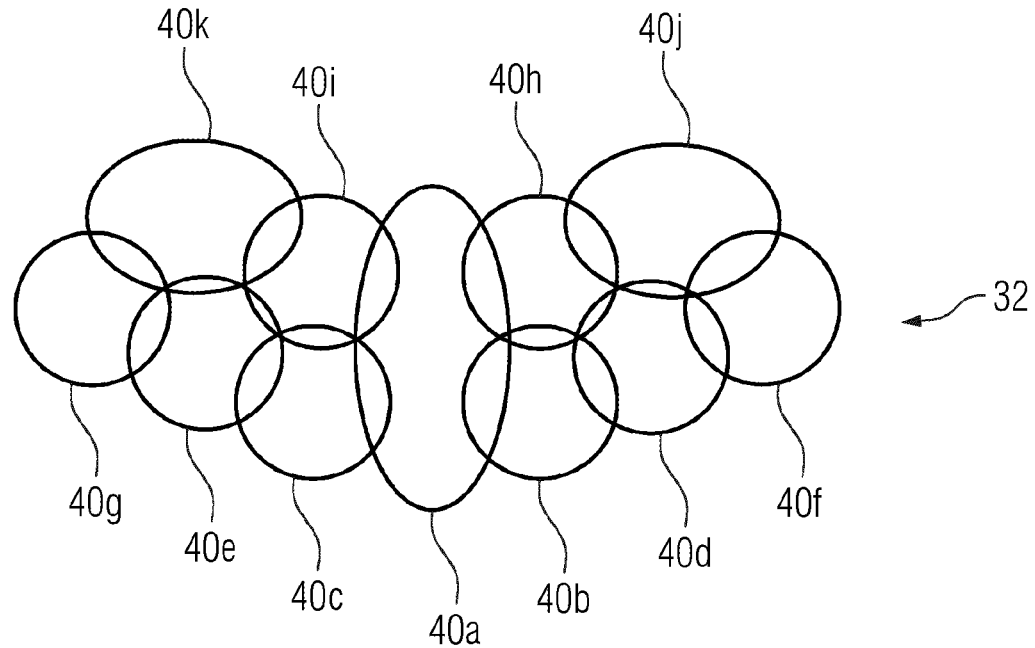
FIG. 12 shows a possible embodiment of a receiver unit of a dental coil according to the disclosure.

FIG. 12 shows a possible arrangement of antennas 32 of a receiver unit of the dental coil 26 according to the disclosure. In this configuration, the array of antennas 32 comprises eleven antennas 40a-k which are disposed in series in a partially overlapping manner along the main extent 33 of the carrier element 30 (cf. FIG. 4). This configuration constitutes a 4-6-1 arrangement. In this arrangement, four antennas 40h-k are disposed along the dental arch of the maxilla, while six antennas 40b-g are disposed along the dental arch of the mandible of the patient 15. The antenna 40a is positioned at an anterior region of the dental arches of the maxilla and the mandible. In particular, the antenna 40a can be positioned centrally at the mouth region and the nose region of the patient 15 when the carrier element 30 (not shown) is positioned for use. In addition, other arrangements of the antennas 40 are self-evidently also conceivable. For example, the signal conductors of individual antennas 40, such as antennas 40j and 40k and/or antennas 40f and 40g, can enclose a larger area compared to antennas 40b-i in order to also cover the temporomandibular joints of the patient 15.

Figure 13:
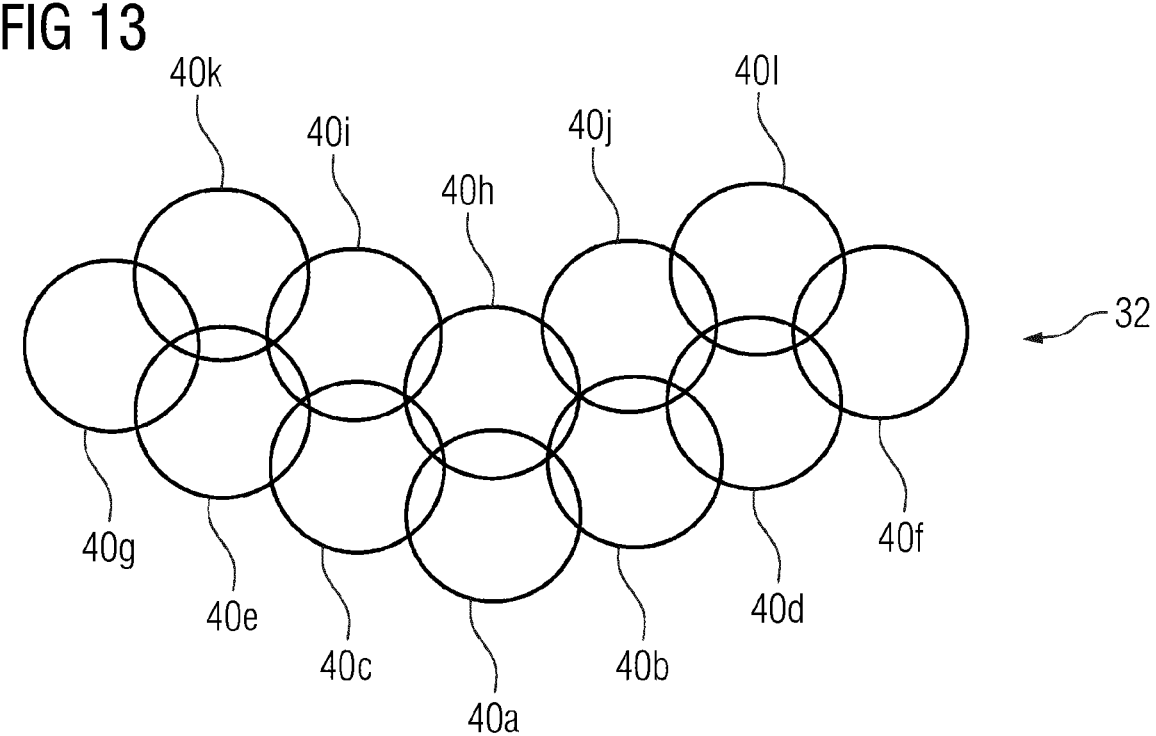
FIG. 13 shows a possible embodiment of a receiver unit of a dental coil according to the disclosure.

FIG. 13 shows another arrangement of antennas 32 of a receiver unit of the dental coil 26 according to the disclosure. In this embodiment, two antennas 40a and 40h are positioned centrally in the area of the mouth region and the nose region of the patient 15 when the carrier element 30 (not shown) is positioned for use. In this case, the array of antennas 32 comprises twelve antennas 40a-1 which are disposed in a 5-7 configuration. In this case, five antennas 40h-1 are disposed along the dental arch of the maxilla of patient 15, while seven antennas 40a-g are disposed along the dental arch of the mandible of the patient.

Figure 14:
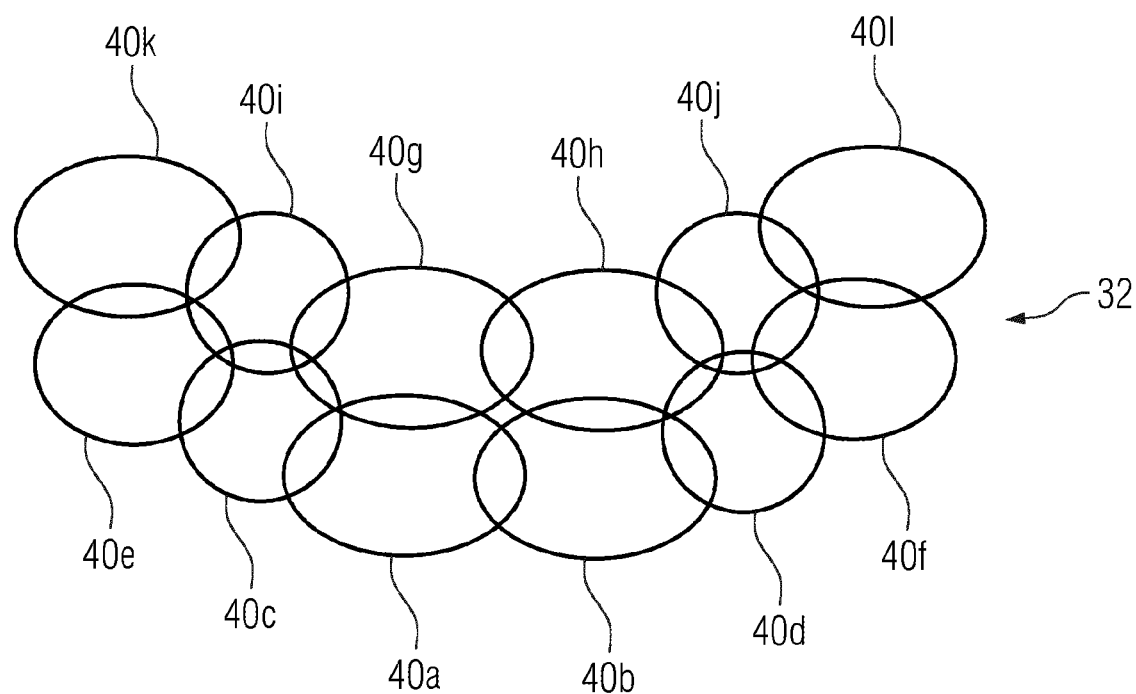
FIG. 14 shows a possible embodiment of a receiver unit of a dental coil according to the disclosure.

FIG. 14 shows another arrangement of antennas 32 of a receiver unit of the dental coil 26 according to the disclosure. In this example, the array of antennas 32 has a 6-6 configuration. Here, the six antennas 40g-1 are disposed along the dental arch of the maxilla of the patient 15 when the carrier element 30 (not shown) is positioned for use, while the six antennas 40a-f are disposed along the dental arch of the mandible of the patient 15. In the area of the mouth region and the nose region of the patient 15, the signal conductors of the antennas 40a, 40b, 40g and 40h overlap so as to allow particularly advantageous bending or adaptation of the antennas 40a, 40b, 40g and 40h to match the outer shape of the jaw region 43 of the patient 15. For example, the array of antennas 32 shown can have at least one articulation 38 that divides the array of antennas 32 into segments along the longitudinal axis of the patient 15. Said articulation 38 can be disposed such that the angle between the pairs of antennas 40a-b and 40g-h can be adjusted. However, it is equally conceivable for the arrays of antennas 32 shown in FIGS. 12 to 14 have articulations 38 at other or additional positions. In addition, the signal conductors of the array of antennas 32 can self-evidently also be made of a flexible material which can be molded to the outer shape of the jaw region 43 of the patient 15. In addition to the embodiments shown, in particular a 3-9 configuration of the array of antennas 32 is also conceivable in which three antennas 40 are disposed along at least part of the dental arch of the maxilla of the patient 15.

Although the disclosure has been illustrated and described in detail by the preferred embodiments, the disclosure is nevertheless not limited by the examples disclosed and other variations will be apparent to persons skilled in the art without departing from the scope of protection sought for the disclosure.

The invention claimed is:

1. A dental coil, comprising:
a transmitter comprising an antenna configured to apply radio frequency (RF) signals in a frequency and power range of a magnetic resonance apparatus to a jaw region of a patient;
a receiver comprising an array of antennas configured to receive magnetic resonance signals from the jaw region of the patient; and
a carrier configured to be placed in a position for use on the jaw region of the patient, and molded to match at least part of an outer shape of the jaw region of the patient; and
an adapter configured to adjust a bending radius of the carrier to adapt a shape of the array of antennas of the receiver to conform to the outer shape of the jaw region of the patient,
wherein the carrier comprises a flexible material and is further configured to maintain the array of antennas of the receiver in a predetermined position with respect to the jaw region of the patient such that the array of antennas of the receiver surrounds the outer shape of the jaw region.

2. The dental coil as claimed in claim 1, wherein the carrier is configured to maintain the antenna of the transmitter in a predetermined position with respect to the jaw region of the patient, and
wherein the transmitter is configured to generate RF signals with a magnetic field strength in a range between 20 µT and 80 µT.

3. The dental coil as claimed in claim 1, wherein:
the transmitter comprises a first antenna and a second antenna, the first antenna and the second antenna being circular and planar and being disposed in parallel-aligned planes spaced from one another, such that a projection of a first surface enclosed by the first antenna along a normal vector of the first surface and a second surface enclosed by the second antenna have a non-empty intersection,
the spacing between the first antenna and the second antenna corresponds to at least a width of the jaw region of the patient,
the normal vector of the first antenna is oriented parallel to a frontal plane of the patient, and
the carrier is configured to maintain the transmitter in a predetermined position with respect to the jaw region of the patient.

4. The dental coil as claimed in claim 1, wherein the carrier is configured to maintain the antenna of the transmitter in a predetermined position with respect to the jaw region of the patient, and
wherein the antenna of the transmitter frames the outer shape of the jaw region of the patient in the predetermined position such that a transmission of RF signals is limited to a volume of the jaw region of the patient.

5. The dental coil as claimed in claim 1, wherein:
the transmitter comprises a first antenna and a second antenna, the first antenna and the second antenna being circular and planar and disposed in parallel-aligned planes spaced from one another, such that a projection of the first surface enclosed by the first antenna along a normal vector of the first surface and a second surface enclosed by the second antenna have a non-empty intersection,
the spacing between the first antenna and the second antenna corresponds to a height of the jaw region of the patient along a longitudinal axis of the patient, and
the normal vector of the first antenna is oriented parallel to a longitudinal axis of the patient in a position of use of the transmitter.

6. The dental coil as claimed in claim 1, further comprising:
a mount configured to hold the carrier in a position of use on the jaw region of the patient,
wherein the carrier and the mount have mutually corresponding plug-in elements that are configured to interconnect the carrier and the mount in a form-fit manner.

7. The dental coil as claimed in claim 6, wherein the mount comprises an electrical connecting cable that is electrically connected to the magnetic resonance apparatus, and
wherein the plug-in elements are configured to electrically connect the antenna of the transmitter and/or the array of antennas of the receiver to the electrical connecting cable of the magnetic resonance apparatus.

8. The dental coil as claimed in claim 1, further comprising:
a mount configured to hold the carrier in a position of use on the jaw region of the patient,
wherein the carrier has an elastic clamp on a side facing away from the patient,
wherein the mount has a frame that flanks a head of the patient on both sides along a section of a longitudinal axis of the patient, and
wherein the carrier is connected to the mount in a position of use on the jaw region of the patient via a force-fit connection between the elastic clamp and the frame.

9. The dental coil as claimed in claim 1, wherein the array of antennas of the receiver are disposed in a row along a main extent of the carrier, and
wherein two adjacent antennas of the array of antennas have an area of overlap along a main extent of the carrier between 0.5 cm to 2 cm.

10. The dental coil as claimed in claim 1, wherein the carrier in a position of use on the jaw region of the patient has a cutout for a nose of the patient, and
wherein an antenna from among the array of antennas of the receiver is disposed such that the antenna flanks a section of the nose of the patient from one side along a longitudinal direction of the patient to receive magnetic resonance signals of a tooth root of an anterior region of the patient.

11. The dental coil as claimed in claim 1, further comprising:
a mount; and
a bite bar,
wherein the mount is configured to hold the carrier in a position of use on the jaw region of the patient, and
wherein the bite bar is mechanically connected to the mount and is configured to align the jaw region of the patient in a predetermined position with respect to the carrier when the bite bar is positioned on a dentition of the patient.

12. A magnetic resonance system, comprising:
a magnetic resonance apparatus; and
a dental coil, comprising:
a transmitter comprising an antenna configured to generate radio frequency (RF) signals in a frequency and power range of a magnetic resonance apparatus to a jaw region of a patient, the generated RF signals having a magnetic field strength in a range between 20 μT and 80 μT;

a receiver comprising an array of antennas configured to receive magnetic resonance signals from the jaw region of the patient; and a carrier configured to be placed in a position for use on the jaw region of the patient, and to maintain the antenna of the transmitter in a predetermined position with respect to the jaw region of the patient, wherein the carrier is molded to match at least part of an outer shape of the jaw region of the patient is further configured to maintain the array of antennas of the receiver in a predetermined position with respect to the jaw region of the patient such that the array of antennas of the receiver surrounds the outer shape of the jaw region, and wherein the magnetic resonance apparatus is configured to acquire magnetic resonance signals of the jaw region of the patient via the dental coil.

13. A dental coil, comprising:
a transmitter comprising an antenna configured to apply radio frequency (RF) signals in a frequency and power range of a magnetic resonance apparatus to a jaw region of a patient;
a receiver comprising an array of antennas configured to receive magnetic resonance signals from the jaw region of the patient; and
a carrier comprising a rigid material and including an articulation dividing the rigid material into segments, the articulation adjusting an angle between two of the segments to set a relative position between at least one segment of the carrier and at least one section of the jaw region of the patient when the carrier is placed in the position for use on the jaw region of the patient,
wherein the carrier is configured to be placed in a position for use on the jaw region of the patient, molded to match at least part of an outer shape of the jaw region of the patient, and to maintain the array of antennas of the receiver in a predetermined position with respect to the jaw region of the patient such that the array of antennas of the receiver surrounds the outer shape of the jaw region.

14. The dental coil as claimed in claim 13, wherein the articulation divides the carrier into two symmetrical halves.

15. A dental coil, comprising:
a transmitter comprising an antenna configured to apply radio frequency (RF) signals in a frequency and power range of a magnetic resonance apparatus to a jaw region of a patient;
a receiver comprising an array of antennas configured to receive magnetic resonance signals from the jaw region of the patient; and
a carrier configured to be placed in a position for use on the jaw region of the patient and molded to match at least part of an outer shape of the jaw region of the patient,
wherein the carrier is further configured to maintain the array of antennas of the receiver in a predetermined position with respect to the jaw region of the patient such that the array of antennas of the receiver surrounds the outer shape of the jaw region,
wherein the array of antennas of the receiver are disposed in a row along a main extent of the carrier, and
wherein two adjacent antennas of the array of antennas have an area of overlap along a main extent of the carrier between 0.5 cm to 2 cm.

* * * * *